(12) United States Patent
Brokx et al.

(10) Patent No.: US 12,404,327 B2
(45) Date of Patent: Sep. 2, 2025

(54) LILRB3-BINDING MOLECULES AND USES THEREFOR

(71) Applicant: UNIVERSITY HEALTH NETWORK, Toronto (CA)

(72) Inventors: Richard Brokx, Toronto (CA); Jacqueline M. Mason, Toronto (CA); Mark R. Bray, Oakville (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 1035 days.

(21) Appl. No.: 17/421,705

(22) PCT Filed: Jan. 16, 2020

(86) PCT No.: PCT/CA2020/050042
§ 371 (c)(1),
(2) Date: Jul. 8, 2021

(87) PCT Pub. No.: WO2020/146946
PCT Pub. Date: Jul. 23, 2020

(65) Prior Publication Data
US 2022/0089723 A1    Mar. 24, 2022

Related U.S. Application Data

(60) Provisional application No. 62/794,064, filed on Jan. 18, 2019.

(51) Int. Cl.
C07K 16/28    (2006.01)

(52) U.S. Cl.
CPC ............................... *C07K 16/2803* (2013.01)

(58) Field of Classification Search
None
See application file for complete search history.

(56) References Cited

U.S. PATENT DOCUMENTS

| | | |
|---|---|---|
| 5,530,101 A | 6/1996 | Queen et al. |
| 5,585,089 A | 12/1996 | Queen et al. |
| 5,693,761 A | 12/1997 | Queen et al. |
| 5,693,762 A | 12/1997 | Queen et al. |
| 5,821,337 A | 10/1998 | Carter et al. |
| 5,859,205 A | 1/1999 | Adair et al. |
| 6,054,297 A | 4/2000 | Carter et al. |
| 6,180,370 B1 | 1/2001 | Queen et al. |
| 6,407,213 B1 | 6/2002 | Carter et al. |
| 7,657,380 B2 | 2/2010 | Lazar et al. |
| 2013/0030156 A1 | 1/2013 | Apostolou et al. |
| 2016/0244525 A1 | 8/2016 | Yin et al. |
| 2018/0201676 A1 | 7/2018 | Blaser et al. |

FOREIGN PATENT DOCUMENTS

| | | |
|---|---|---|
| CN | 107530402 A | 1/2018 |
| CN | 107660150 A | 2/2018 |
| JP | 2013-517330 A | 5/2013 |
| JP | 2013-517331 A | 5/2013 |
| WO | WO 92/11018 A1 | 7/1992 |
| WO | WO 2011091177 A1 | 7/2011 |
| WO | WO 2011091181 A1 | 7/2011 |
| WO | WO 2013/136193 A2 | 9/2013 |
| WO | WO 2013/181438 A3 | 12/2013 |
| WO | WO 2015/000059 A1 | 1/2015 |
| WO | WO 2016127247 A1 | 8/2016 |
| WO | WO 2018119425 A2 | 6/2018 |

OTHER PUBLICATIONS

Nowak, Immunol. Rev. vol. 276: 66-79 Scott, 2012, Nature Reviews, vol. 12: 278-287.*
Zeller, 2023, Front. Immunol. pp. 1-14 Beers, 2016, Blood. vol. 127: 1097-1101.*
Chen, 2018, J. Clin. Invest. vol. 12: 5647-5662 Chan, 2010, Nat. Rev. vol. 10: 301-316.*
Hirayasu, 2015, J. Human. Genetics vol. 60: 703-708.*
International Search Report and Written Opinion mailed Apr. 24, 2020 in International Application No. PCT/CA20/50195.
Jefferis, Roy et al., "Interaction sites on human IgG-Fc for FcgR: current models," Immunol. Lett., 2002, 82:57-65.
Ye, Jian et al., "IgBLAST: an immunoglobulin variable domain sequence analysis tool," Nucleic Acids Research, 2013, 41:W34-W40.
Huang, J. et al., "Leukocyte Immunoglobulin-Like Receptors Maintain Unique Antigen-Presenting Properties of Circulating Myeloid Dendritic Cells in HIV-1-Infected Elite Controllers," Journal of Virology, Sep. 2010, 84(18):9463-9471.
Baca, Manuel et al., "Antibody Humanization Using Monovalent Phage Display," J. Biol. Chem., Apr. 18, 1997, 272(16):10678-10684.
Baeuerle, Patrick A. et al., "NF-κB: Ten Years After," Cell, Oct. 4, 1996, 87:13-20.
Baldwin, Albert S., Jr. et al., "The NF-κB and IκB Proteins: New Discoveries and Insights," Ann. Rev. Immunol., 1996, 12:141.
Carter, Paul et al., "Humanization of an anti-p185$^{HER2}$ antibody for human cancer therapy," Proc. Natl. Acad. Sci. USA, May 1992, 89:4285-4289.
Dayhoff, Margaret O., "Atlas of Protein Sequence and Structure," National Biomedical Research Foundation, 1978, 5(3):353-358.
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., 2002, 169:3076-3084.
Edelman, Gerald M. et al., "The Covalent Structure of an Entire γG Immunoglobulin Molecule," Proc. Natl. Acad. Sci. USA, Mar. 21, 1969, 63:78-85.

(Continued)

*Primary Examiner* — Amy E Juedes
(74) *Attorney, Agent, or Firm* — Morgan, Lewis & Bockius LLP

(57) ABSTRACT

The invention provides novel anti-LILRB3 antibodies, pharmaceutical compositions comprising such antibodies, and therapeutic methods of using such antibodies and pharmaceutical compositions for the treatment of diseases such as cancer, autoimmune disease, or allergic inflammation. This invention can also be used to modulate osteoclast differentiation.

20 Claims, 5 Drawing Sheets

Specification includes a Sequence Listing.

(56) References Cited

OTHER PUBLICATIONS

Gorman, Scott D. et al., "Reshaping a therapeutic CD4 antibody," Proc. Natl. Acad. Sci. USA, May 1991, 88:4181-4185.

Gribskov, Michael et al., "Sigma factors from E. coli, B. subtilis, phage SP01, and phage T4 are homologous proteins," Nucl. Acids Res., 1986, 14(6):6745-6763.

He, Xing-Yue et al., "Humanization and Pharmacokinetics of a Monoclonal Antibody with Specificity for Both E- and P-Selectin," J. Immunol., 1998, 160: 1029-1035.

Jones, Peter T. et al., "Replacing the complementarity-determining regions in a human antibody with those from a mouse," Nature, May 29, 1986, 321:522-525.

Krauss, Jürgen et al., "Specificity grafting of human antibody frameworks selected from a phage display library: generation of a highly stable humanized anti-CD22 single-chain Fv fragment," Protein Engineering, 2003, 16(10):753-759.

Langer, Robert, "New Methods of Drug Delivery," Sep. 28, 1990, Science, 249:1527-1533.

O'Connor, Shane J. et al., "Humanization of an antibody against human protein C and calcium-dependence involving framework residues," Protein Engineering, 1998, 11(4):321-328.

Presta, Leonard G. et al., "Humanization of an Anti-Vascular Endothelial Growth Factor Monoclonal Antibody for the Therapy of Solid Tumors and Other Disorders," Cancer Res., Oct. 15, 1997, 57(20):4593-4599.

Queen, Cary et al., "A humanized antibody that binds to the interleukin 2 receptor," Dec. 1989, Proc. Natl. Acad. Sci, USA, 86:10029-10033.

Rader, Christoph et al., "A phage display approach for rapid antibody humanization: Designed combinatorial V gene libraries," Proc. Natl. Acad. Sci. USA, Jul. 1998, 95: 8910-8915.

Riechmann, Lutz et al., "Reshaping human antibodies for therapy," Nature, Mar. 24, 1988, 332:323-327.

Roguska, Michael A. et al., "Humanization of murine monoclonal antibodies through variable domain resurfacing," Proc. Natl. Acad. Sci. USA, Feb. 1994, 91:969-973.

Roque, A. Cecília A et al., "Antibodies and Genetically Engineered Related Molecules: Production and Purification," 2004, Biotechnol. Prog., 20:639-654.

Rosok, Mae Joanne et al., "A Combinatorial Library Strategy for the Rapid Humanization of Anticarcinoma BR96 Fab," J. Biol. Chem, Sep. 13, 1996, 271(37): 22611-22618.

Schmitz, Gerd et al., "Pharmacogenomics: implications for laboratory medicine," Clinica Chimica Acta, 2001, 308:43-53.

Smith, Temple F. et al., "Comparison of Biosequences," Advances in Applied Mathematics, 1981, 2:482-489.

Steimer, Werner et al., "Pharmacogenetics: a new diagnostic tool in the management of antidepressive drug therapy," Clinica Chimica Acta, 2001, 308: 33-41.

Tan, Philip et al., "'Superhumanized' Antibodies: Reduction of Immunogenic Potential by Complementarity-Determining Region Grafting with Human Germline Sequences: Application to an Anti-CD28," J. Immunol., 2002, 169:1119-1125.

Tsurushita, Naoya, et al., "Humanization of Monoclonal Antibodies," Molecular Biology of B Cells, Elsevier Science (USA), 2004, 533-545.

Verhoeyen, Martine et al., "Reshaping Human Antibodies: Grafting an Antilysozyme Activity," Science, Mar. 25, 1988, 239:1534-1536.

Wu, Herren et al., "Humanization of a Murine Monoclonal Antibody by Simultaneous Optimization of Framework and CDR Residues," 1999, J. Mol. Biol. 294:151-162.

Xu, Jie et al., "Research progress on biological functions of leukocyte immunoglobulin-like receptor subfamily B," Journal of Xinxiang Medical College, Sep. 2018, 35(9):835-839.

\* cited by examiner

LILRB3-BINDING MOLECULES AND USES THEREFOR

CROSS REFERENCE TO RELATED APPLICATION

The present application claims the benefit of priority to U.S. Provisional Application No. 62/794,064, filed Jan. 18, 2019, the contents of which is expressly incorporated herein in its entirety for all purposes.

SEQUENCE LISTING

The present application contains a Sequence Listing which has been submitted electronically in ASCII format and is hereby incorporated by reference in its entirety. Said ASCII copy, created on Jan. 15, 2020, is named 011506-5022_ST25.txt and is 72 kilobytes in size.

TECHNICAL FIELD

The present disclosure relates to antibodies that specifically bind to LILRB3, e.g., human LILRB3 (hLILRB3), and pharmaceutical compositions comprising such LILRB3-binding antibodies thereof. Methods of using the antibodies of the invention to detect human LILRB3 or to modulate human LILRB3 activity in the treatment of various diseases, including inflammatory diseases, autoimmune diseases and cancer, are also encompassed by the invention.

BACKGROUND OF THE INVENTION

The human leukocyte Ig-like receptor (LILR) family belongs to the superfamily of paired receptors that have the potential to transmit stimulatory or inhibitory signals according to the presence or absence of tyrosine-based signaling motifs in their cytoplasmic tail. Human LILRs consist of five stimulatory receptors (LILRA1-5), six inhibitory receptors (LILRB1-6) and two pseudogenes. LILRs are expressed on various cells, such as lymphoid and myeloid cells, and the expression patterns are different from receptor to receptor. Polymorphism and copy-number variation contribute to diversity within humans. In general, LILR activity can result in the upregulation or downregulation of both innate and adaptive immune functions with a range of effects on different cell types. Recent studies have found that several LILRB family members are expressed by cancer cells, in particular hematopoietic cancer cells, and may support cancer development and relapse, as well as the activity of cancer stem cells.

Human LILRB3 (also called CD85A, ILT5, LIR3 or HL9) contains 4 extracellular immunoglobulin domains, a transmembrane domain and 4 cytoplasmic immunoreceptor tyrosine-based inhibition motifs (ITIMs). Expression of LILRB3 has been reported on monocytes, monocyte-derived osteoclasts, granulocytes, dendritic cells, osteoclasts and progenitor mast cells. The ligand for LILRB3 has not been identified, and little is known about the function of LILRB3. Collectively, these findings suggest that the development of agents useful in modulating signaling from LILRB3 would be of great benefit in diseases involving dysregulation of the immune system, including inflammatory diseases, autoimmune diseases and cancer.

SUMMARY OF THE INVENTION

In one aspect, the present invention relates to novel anti-LILRB3 antibodies. In some embodiments, the anti-LILRB3 antibodies include a heavy chain variable region comprising an amino acid sequence of SEQ ID NO:1 and a light chain variable region comprising an amino acid sequence of SEQ ID NO:2. In some embodiments, the anti-LILRB3 antibodies include a heavy chain variable region comprising an amino acid sequence of SEQ ID NO:3 and a light chain variable region comprising an amino acid sequence of SEQ ID NO:4. In some embodiments, the anti-LILRB3 antibodies include a heavy chain variable region comprising an amino acid sequence of SEQ ID NO:5 and a light chain variable region comprising an amino acid sequence of SEQ ID NO:6. In some embodiments, the anti-LILRB3 antibodies include a heavy chain variable region comprising an amino acid sequence of SEQ ID NO:7 and a light chain variable region comprising an amino acid sequence of SEQ ID NO: 8. In some embodiments, the anti-LILRB3 antibodies include a heavy chain variable region comprising an amino acid sequence of SEQ ID NO:9 and a light chain variable region comprising an amino acid sequence of SEQ ID NO:10. In some embodiments, the anti-LILRB3 antibodies include a heavy chain variable region comprising an amino acid sequence of SEQ ID NO:11 and a light chain variable region comprising an amino acid sequence of SEQ ID NO:12. In some embodiments, the anti-LILRB3 antibodies include a heavy chain variable region comprising an amino acid sequence of SEQ ID NO:13 and a light chain variable region comprising an amino acid sequence of SEQ ID NO:14. In some embodiments, the anti-LILRB3 antibodies include a heavy chain variable region comprising an amino acid sequence of SEQ ID NO:15 and a light chain variable region comprising an amino acid sequence of SEQ ID NO:16. In some embodiments, the anti-LILRB3 antibodies include a heavy chain variable region comprising an amino acid sequence of SEQ ID NO:17 and a light chain variable region comprising an amino acid sequence of SEQ ID NO:18. In some embodiments, the anti-LILRB3 antibodies include a heavy chain variable region comprising an amino acid sequence of SEQ ID NO:19 and a light chain variable region comprising an amino acid sequence of SEQ ID NO:20. In some embodiments, the anti-LILRB3 antibodies include a heavy chain variable region comprising an amino acid sequence of SEQ ID NO:21 and a light chain variable region comprising an amino acid sequence of SEQ ID NO:22. In some embodiments, the anti-LILRB3 antibodies include a heavy chain variable region comprising an amino acid sequence of SEQ ID NO:23 and a light chain variable region comprising an amino acid sequence of SEQ ID NO:24. In some embodiments, the anti-LILRB3 antibodies include a heavy chain variable region comprising an amino acid sequence of SEQ ID NO:25 and a light chain variable region comprising an amino acid sequence of SEQ ID NO:26.

In some embodiments, the anti-LILRB3 antibodies include a vhCDR1 comprising SEQ ID NO:27, a vhCDR2 comprising SEQ ID NO:28, a vhCDR3 comprising SEQ ID NO: 29, a vlCDR1 comprising SEQ ID NO:30, a vlCDR2 comprising STS, and a vlCDR3 comprising SEQ ID NO:32. In some embodiments, the anti-LILRB3 antibodies include a vhCDR1 comprising SEQ ID NO:33, a vhCDR2 comprising SEQ ID NO: 34, a vhCDR3 comprising SEQ ID NO:35, a vlCDR1 comprising SEQ ID NO:36, a vlCDR2 comprising STS, and a vlCDR3 comprising SEQ ID NO:38. In some embodiments, the anti-LILRB3 antibodies include a vhCDR1 comprising SEQ ID NO: 39, a vhCDR2 comprising SEQ ID NO:40, a vhCDR3 comprising SEQ ID NO:41, a vlCDR1 comprising SEQ ID NO:42, a vlCDR2 comprising NAK, and a vlCDR3 comprising SEQ ID NO:44. In some embodiments, the anti-LILRB3 antibodies include a vhCDR1 comprising SEQ ID NO:45, a vhCDR2 comprising SEQ ID NO:46, a vhCDR3 comprising SEQ ID NO:47, a vlCDR1 comprising SEQ ID NO:48, a vlCDR2 comprising WAS, and a vlCDR3 comprising SEQ ID NO:50. In some embodiments, the anti-LILRB3 antibodies include a vhCDR1 comprising SEQ ID NO:51, a vhCDR2 comprising SEQ ID NO:52, a vhCDR3 comprising SEQ ID NO:53, a vlCDR1 comprising SEQ ID NO:54, a vlCDR2 comprising STS, and a vlCDR3 comprising SEQ ID NO:56. In some embodiments, the anti-LILRB3 antibodies include avhCDR1 comprising SEQ ID NO:57, a vhCDR2 comprising SEQ ID NO:58, a vhCDR3 comprising SEQ ID NO:59, a vlCDR1 comprising SEQ ID NO:60, a vlCDR2 comprising STS, and a vlCDR3 comprising SEQ ID NO:62. In some embodiments, the anti-LILRB3 antibodies include a vhCDR1 comprising SEQ ID NO: 63, a vhCDR2 comprising SEQ ID NO:64, a vhCDR3 comprising SEQ ID NO:65, a vlCDR1 comprising SEQ ID NO:66, a vlCDR2 comprising STS, and a vlCDR3 comprising SEQ ID NO:68. In some embodiments, the anti-LILRB3 antibodies include a vhCDR1 comprising SEQ ID NO:69, avhCDR2 comprising SEQ ID NO:70, a vhCDR3 comprising SEQ ID NO:71, a vlCDR1 comprising SEQ ID NO:72, a vlCDR2 comprising STS, and a vlCDR3 comprising SEQ ID NO:74. In some embodiments, the anti-LILRB3 antibodies include a vhCDR1 comprising SEQ ID NO:75, a vhCDR2 comprising SEQ ID NO:76, a vhCDR3 comprising SEQ ID NO:77, a vlCDR1 comprising SEQ ID NO: 78, a vlCDR2 comprising TTS, and a vlCDR3 comprising SEQ ID NO: 80. In some embodiments, the anti-LILRB3 antibodies include avhCDR1 comprising SEQ ID NO:81, a vhCDR2 comprising SEQ ID NO:82, a vhCDR3 comprising SEQ ID NO:83, a vlCDR1 comprising SEQ ID NO:84, a vlCDR2 comprising STS, and a vlCDR3 comprising SEQ ID NO:86. In some embodiments, the anti-LILRB3 antibodies include a vhCDR1 comprising SEQ ID NO: 87, a vhCDR2 comprising SEQ ID NO: 88, a vhCDR3 comprising SEQ ID NO: 89, a vlCDR1 comprising SEQ ID NO: 90, a vlCDR2 comprising STS, and a vlCDR3 comprising SEQ ID NO:92. In some embodiments, the anti-LILRB3 antibodies include a vhCDR1 comprising SEQ ID NO:93, a vhCDR2 comprising SEQ ID NO:94, a vhCDR3 comprising SEQ ID NO:95, a vlCDR1 comprising SEQ ID NO:96, a vlCDR2 comprising STS, and a vlCDR3 comprising SEQ ID NO:98. In some embodiments, the anti-LILRB3 antibodies include a vhCDR1 comprising SEQ ID NO:99, a vhCDR2 comprising SEQ ID NO: 100, a vhCDR3 comprising SEQ ID NO:101, a vlCDR1 comprising SEQ ID NO: 102, a vlCDR2 comprising STS, and a vlCDR3 comprising SEQ ID NO: 104.

In some embodiments, the anti-LILRB3 antibodies described herein bind human LILRB3.

In another aspect, the present invention relates to a nucleic acid composition encoding any one of the anti-LILRB3 antibodies described herein.

Another aspect of the present invention relates to an expression vector composition that includes any one of the nucleic acid compositions described herein. In some embodiments, the first nucleic acid is contained in a first expression vector and the second nucleic acid is contained in a second expression vector. In some other embodiments, the first nucleic acid and the second nucleic acid are contained in a single expression vector.

Another aspect of the present invention relates to a host cell that includes any one of the expression vectors described herein. Also presented is a method of making anti-LILRB3 antibodies, and the method includes culturing the host cell under conditions wherein the antibodies expressed, and recovering the antibodies.

In another aspect, the present invention relates to a composition that includes any one of the anti-LILRB3 antibodies described herein, and a pharmaceutical acceptable carrier or diluent.

Also described is a method of modulating an immune response in a subject, and the method includes administering to the subject an effective amount of any one of the anti-LILRB3 antibodies described herein, or any one of the compositions described herein. In some embodiments, the method includes administering to the subject an effective amount of an anti-LILRB3 antibody that serves as a LILRB3 antagonist, or a pharmaceutical composition thereof. In some embodiments, the method includes administering to the subject an effective amount of an anti-LILRB3 antibody that serves as a LILRB3 agonist, or a pharmaceutical composition thereof.

In another aspect, the present invention relates to a method of treating cancer in a subject, and the method includes administering to the subject an effective amount of an anti-LILRB3 antibody described herein or any one of the compositions described herein. In some embodiments, the cancer to be treated upregulates LILRB3 compared to the corresponding non-cancerous tissue. In some embodiments, the subject to be treated expresses a high level of LILRB3 on hematopoietic cells. The cancer to be treated can be any cancer. In some embodiments, an anti-LILRB3 antibody is used in combination with one or more additional therapeutic agents to treat cancer. In some embodiments, such anti-cancer therapeutic agents are other immune checkpoint inhibitors, such as Ipilimumab, Nivolumab, Pembrolizumab, Avelumab, Durvalumab, and Atezolizumab.

In another aspect, the present invention relates to a method of treating an autoimmune disease in a subject, and the method includes administering to the subject an effective amount of any one of the anti-LILRB3 antibodies described herein, or any one of the compositions described herein.

In another aspect, the present invention relates to a method of treating an autoimmune disease in a subject, and the method includes administering to the subject an effective amount of an anti-LILRB3 antibody described herein, or any one of the compositions described herein.

In a further aspect, the present invention relates to a method of treating allergic inflammation in a subject, and the method includes administering to the subject an effective amount of any one of the anti-LILRB3 antibodies described herein, or any one of the compositions described herein.

In a further aspect, the present invention relates to a method of modulating osteoclast differentiation, and the method includes administering to the subject an effective amount of any one of the anti-LILRB3 antibodies described herein, or any one of the compositions described herein.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1A:
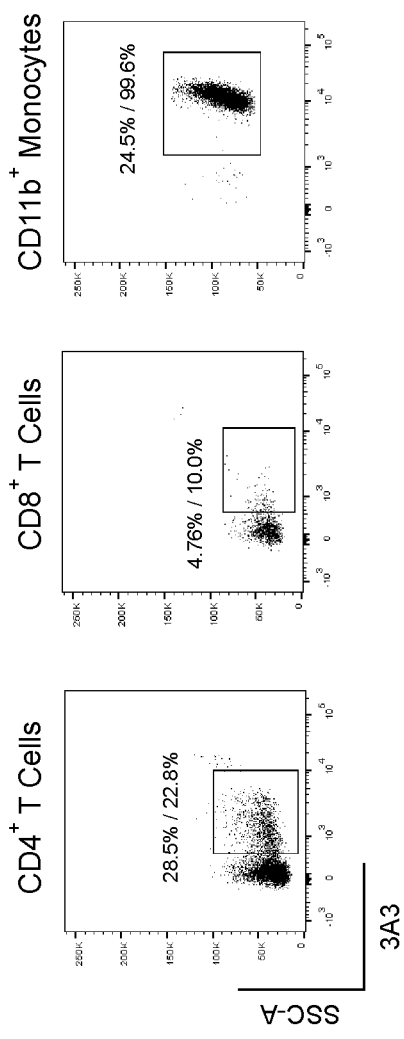
FIG. 1A and FIG. 1B show LILBR3 surface expression on various hematopoietic subsets using flow cytometry.

The present disclosure provides novel anti-LILRB3 antibodies. In some embodiments, the anti-LILRB3 antibodies act to modulate an immune response in a subject, and, for example, to treat cancer or an autoimmune disease. In some embodiments the anti-LILRB3 antibodies act to treat allergic inflammation. In some embodiments the anti-LILRB3 antibodies modulate osteoclast differentiation.

To facilitate an understanding of the present invention, a number of terms and phrases are defined below.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

By "antigen binding domain" or "ABD" herein is meant a set of six Complementary Determining Regions (CDRs) that, when present as part of a polypeptide sequence, specifically binds a target antigen as discussed herein. Thus, an "antigen binding domain" binds a target antigen as outlined herein. As is known in the art, these CDRs are generally present as a first set of variable heavy CDRs (vhCDRs or VHCDRs or CDR-HC) and a second set of variable light CDRs (vlCDRs or VLCDRs or CDR-LC), each comprising three CDRs: vhCDR1, vhCDR2, vhCDR3 for the heavy chain and vlCDR1, vlCDR2 and vlCDR3 for the light chain. The CDRs are present in the variable heavy and variable light domains, respectively, and together form an Fv region. Thus, in some cases, the six CDRs of the antigen binding domain are contributed by a variable heavy and variable light chain. In a "Fab" format, the set of 6 CDRs are contributed by two different polypeptide sequences, the variable heavy domain (vh or VH; containing the vhCDR1, vhCDR2 and vhCDR3) and the variable light domain (vl or VL; containing the vlCDR1, vlCDR2 and vlCDR3), with the C-terminus of the vh domain being attached to the N-terminus terminus of the CH1 domain of the heavy chain and the C-terminus of the vl domain being attached to the N-terminus of the constant light domain (and thus forming the light chain). In a scFv format, the VH and VL domains are covalently attached, generally through the use of a linker as outlined herein, into a single polypeptide sequence, which can be either (starting from the N-terminus) vh-linker-vl or vl-linker-vh, with the former being generally preferred (including optional domain linkers on each side, depending on the format used. As is understood in the art, the CDRs are separated by framework regions in each of the variable heavy and variable light domains: for the light variable region, these are FR1-vlCDR1-FR2-vlCDR2-FR3-vlCDR3-FR4, and for the heavy variable region, these are FR1-vhCDR1-FR2-vhCDR2-FR3-vhCDR3-FR4, with the framework regions showing high identity to human germline sequences. Antigen binding domains of the invention include, Fab, Fv and scFv.

The term "antibody" is used in the broadest sense and includes, for example, an intact immunoglobulin or an antigen binding portion. Antigen binding portions may be produced by recombinant DNA techniques or by enzymatic or chemical cleavage of intact antibodies. Thus the term antibody includes traditional tetrameric antibodies of two heavy chains and two light chains, as well as antigen binding fragments such as Fv, Fab and scFvs. In some cases, the invention provides bispecific antibodies that include at least one antigen binding domain as outlined herein.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g., the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution M252Y refers to a variant polypeptide, in this case an Fc variant, in which the methionine at position 252 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g., from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4. The protein variant sequence herein will preferably possess at least about 80% identity with a parent protein sequence, and most preferably at least about 90% identity, more preferably at least about 95%-98%-99% identity. Variant protein can refer to the variant protein itself, compositions comprising the protein variant, or the DNA sequence that encodes it.

Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. Thus, for example M252Y or 252Y is an Fc variant with the substitution tyrosine at position 252 relative to the parent Fc polypeptide, wherein the numbering is according to the EU index. Likewise, M252Y/S254T/T256E defines an Fc variant with the substitutions M252Y, S254T and T256E relative to the parent Fc polypeptide. The identity of the wild type amino acid may be unspecified, in which case the aforementioned variant is referred to as 252Y/254T/256E. It is noted that the order in which substitutions are provided is arbitrary, that is to say that, for example, 252Y/254T/256E is the same Fc variant as 254T/252Y/256E, and so on. For all positions discussed in the present invention that relate to antibodies, unless otherwise noted, amino acid position numbering is according to Kabat for the variable region numbering and is according to the EU index for the constant regions, including the Fc region. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids.

As used herein, "protein" herein is meant at least two covalently attached amino acids, which includes proteins, polypeptides, oligopeptides and peptides. The peptidyl group may comprise naturally occurring amino acids and peptide bonds.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein.

By "Fv" or "Fv fragment" or "Fv region" as used herein is meant a polypeptide that comprises the VL and VH domains of a single antigen binding domain (ABD). As will be appreciated by those in the art, these generally are made up of two chains, or can be combined (generally with a linker as discussed herein) to form a scFv.

By "amino acid" and "amino acid identity" as used herein is meant one of the 20 naturally occurring amino acids that are coded for by DNA and RNA.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "heavy constant region" herein is meant the CH1-hinge-CH2-CH3 portion of an antibody, generally from human IgG1, IgG2 or IgG4.

By "target antigen" as used herein is meant the molecule that is bound specifically by the variable region of a given antibody. In the present case, the target antigen is a LILRB3 protein.

By "target cell" as used herein is meant a cell that expresses a target antigen.

By "variable region" as used herein is meant the region of an immunoglobulin that comprises one or more Ig domains substantially encoded by any of the *V.kappa.*, *V.lamda.*, and/or VH genes that make up the *kappa*, *lambda*, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

By "position" as used herein is meant a location in the sequence of a protein. Positions may be numbered sequentially, or according to an established format, for example the EU index for antibody numbering.

By "residue" as used herein is meant a position in a protein and its associated amino acid identity. For example, Asparagine 297 (also referred to as Asn297 or N297) is a residue at position 297 in the protein sequence.

The antibodies of the present invention are generally recombinant. "Recombinant" means the antibodies are generated using recombinant nucleic acid techniques in exogenous host cells.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs [0279] to [0280] of US Pub. No. 20160244525, hereby incorporated by reference. Another approximate alignment for nucleic acid sequences is provided by the local homology algorithm of Smith and Waterman, Advances in Applied Mathematics, 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986).

An example of an implementation of this algorithm to determine percent identity of a sequence is provided by the Genetics Computer Group (Madison, WI) in the "BestFit" utility application. The default parameters for this method are described in the Wisconsin Sequence Analysis Package Program Manual, Version 8 (1995) (available from Genetics Computer Group, Madison, WI). Another method of establishing percent identity in the context of the present invention is to use the MPSRCH package of programs copyrighted by the University of Edinburgh, developed by John F. Collins and Shane S. Sturrok, and distributed by Intelli-Genetics, Inc. (Mountain View, CA). From this suite of packages, the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the internet address located by placing http:// in front of blast.ncbi.nlm.nih.gov/Blast.cgi.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

In some embodiments, two or more amino acid sequences are at least 50%, 60%, 70%, 80%, or 90% identical. In some embodiments, two or more amino acid sequences are at least 95%, 97%, 98%, 99%, or even 100% identical.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of Kd to Ka (i.e., Kd/Ka) and is expressed as a molar concentration (M). $K_D$ values for antibodies can be determined using methods well established in the art. In some embodiments, the method for determining the $K_D$ of an antibody is by using surface plasmon resonance, for example, by using a biosensor system such as a BIACORE® system. In some embodiments, the $K_D$ of an antibody is determined by Bio-Layer Interferometry. In some embodiments, the $K_D$ value is measured with the immobilized. In other embodiments, the $K_D$ value is measured with the antibody (e.g., parent mouse antibody, chimeric antibody, or humanized antibody variants) immobilized. In certain embodiments, the $K_D$ value is measured in a bivalent binding mode. In other embodiments, the $K_D$ value is measured in a monovalent binding mode.

A "disease" includes a state of health of an animal, including a human, wherein the animal cannot maintain homeostasis, and wherein if the disease is not ameliorated then the animal's health continues to deteriorate.

In contrast, a "disorder" in an animal, including a human, includes a state of health in which the animal is able to maintain homeostasis, but in which the animal's state of health is less favorable than it would be in the absence of the disorder. Left untreated, a disorder does not necessarily cause a further decrease in the animal's state of health.

The terms "treatment", "treating", "treat", and the like, refer to obtaining a desired pharmacologic and/or physiologic effect. The effect may be prophylactic in terms of completely or partially preventing a disease or symptom thereof or reducing the likelihood of a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

As used herein, the term "mammal" refers to any mammal, including, but not limited to, mammals of the order Rodentia, such as mice and hamsters, and mammals of the order Logomorpha, such as rabbits. In some embodiments, the mammals are from the order Carnivora, including felines (cats) and canines (dogs). In some embodiments, the mammals are from the order Artiodactyla, including bovines (cows) and swines (pigs) or of the order Perssodactyla, including Equines (horses). It is most preferred that the mammals are of the order Primates, Ceboids, or Simoids (monkeys) or of the order Anthropoids (humans and apes). In some embodiments, the mammal is a human. In some embodiments, the mammal is cynomolgus monkey.

The term "regression," as well as words stemming therefrom, as used herein, does not necessarily imply 100% or complete regression. Rather, there are varying degrees of regression of which one of ordinary skill in the art recognizes as having a potential benefit or therapeutic effect. In this respect, the disclosed methods can provide any amount of any level of regression of a cancer in a mammal. Furthermore, the regression provided by the inventive method can include regression of one or more conditions or symptoms of the disease, e.g., a cancer. Also, for purposes herein, "regression" can encompass delaying the onset of the disease, delaying the onset of a symptom, and/or delaying the onset of a condition thereof. With respect to progressive diseases and disorders, "regression" can encompass slowing the progression of the disease or disorder, slowing the progression of a symptom of the disease or disorder, and/or slowing the progression of a condition thereof.

An "effective amount" or "therapeutically effective amount" of a composition includes that amount of the composition which is sufficient to provide a beneficial effect to the subject to which the composition is administered. An "effective amount" of a delivery vehicle includes that amount sufficient to effectively bind or deliver a composition.

By "individual" or "host" or "subject" or "patient" is meant any mammalian subject for whom diagnosis, treatment, or therapy is desired, particularly humans. Other subjects may include cynomolgus monkey, cattle, dogs, cats, guinea pigs, rabbits, rats, mice, horses, and so on.

The term "in combination with" as used herein refers to uses where, for example, a first therapy is administered during the entire course of administration of a second therapy; where the first therapy is administered for a period of time that is overlapping with the administration of the second therapy, e.g., where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The term "allergic inflammation" as used herein refers to a local or general hypersensitivity reaction to at least one particular allergens. "Allergic inflammation" symptoms can vary greatly in effects and intensity.

"Encoding" includes the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if, for example, transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "nucleic acid" includes RNA or DNA molecules having more than one nucleotide in any form including single-stranded, double-stranded, oligonucleotide or polynucleotide. The term "nucleotide sequence" includes the ordering of nucleotides in an oligonucleotide or polynucleotide in a single-stranded form of nucleic acid.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes including non-native nucleic acid sequences, and the like.

The term "operably linked" as used herein includes a polynucleotide in functional relationship with a second polynucleotide, e.g., a single-stranded or double-stranded nucleic acid moiety comprising the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region. The order specified when indicating operably linkage is not important. For example, the phrases: "the promoter is operably linked to the nucleotide sequence" and "the nucleotide sequence is operably linked to the promoter" are used interchangeably herein and are considered equivalent. In some cases, when the nucleic acid encoding the desired protein further comprises a promoter/regulatory sequence, the promoter/regulatory sequence is positioned at the 5' end of the desired protein coding sequence such that it drives expression of the desired protein in a cell.

The terms "oligonucleotide," "polynucleotide," and "nucleic acid molecule", used interchangeably herein, refer to a polymeric forms of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

The term "osteoclast" as used herein is a large multinucleated cell with abundant acidophilic cytoplasm derived from hematopoietic stem cells, functioning in the absorption and removal of osseous tissue.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

Various aspects of the invention are set forth below in sections; however, aspects of the invention described in one particular section are not to be limited to any particular section.

I. Antibodies

The present disclosure provides novel anti-LILRB3 antibodies. Such antibodies bind to and/or affect the functional properties of human LILRB3. Table 1 lists peptide sequences of heavy chain variable regions and light chain variable regions that, in combination as designated in Table 1, are LILRB3 antibodies. In some embodiments, the heavy chain variable region and the light chain variable region are arranged in a Fab format. In some embodiments, the heavy chain variable region and the light chain variable region are fused together to from an scFv.

TABLE 1

| Clone | Heavy chain variable region amino acid sequence | Light chain variable region amino acid sequence |
|---|---|---|
| 2E1 | MEWPCIFLFLLSVTEGVHSQVQL QQSGPELVKPGASVKISCKASDY AFSSSWMNWVKQRPGKGLEWIG RIYPGDGDTNYNGKFKGKATLT ADKSSSTAYMQLSSLTSEDSAVY FCAREIYYDYDGYFDVWGTGTT VTVSSAKTTPPSVYPLAPGSAAQ TNSMVTLGCLVKGYFPEPVTVT WNSGSLSSGVHTFPAVLQSDLYT LSSSVTVPSSTWPSQTVTCNVAH PASSTKVDKKIVPRDCGCKPCIC TVPEVSSVFIFPPKPKDVLTITLTP KVTCVVVDISKDDQ SEQ ID NO: 1(IgG1) CDR1 (SEQ ID NO: 27)- DYAF S S SW CDR2 (SEQ ID NO: 28)- IYPGDGDT CDR3 (SEQ ID NO: 29)- AREIYYDYDGYFDV | MHFQVQIFSFLLISASVIMSRGQ IVLTQSPAIMSASPGEKVTITCS ASSSVNYMHWFQQKSGTSPKL WIYSTSNLASGVPARFSGSGSG TSYSLTISRMEAEDAATYYCQQ RSSYPYTFGGGTKLEIKRADAA PTVSIFPPSSEQLTSGGASVVCF LNNFYPRDINVKWKIDGSERQN GVLNSWTDQDSKDSTYSMSST LTLTKDEYERHNSYTCEATHKT STSPR SEQ ID NO: 2 (kappa) CDR1 (SEQ ID NO: 30)-SSVNY CDR2 -STS CDR3 (SEQ ID NO: 32)- CQQRSSYPY |
| 3A3 | MEWTWVFLFLLSVTAGVHSQVQ LQQSRTELMKPGASVKLSCKAT GYTFTGYWIEWVKQRPGHGLEW IGEILPGSTNINYNERFKGKATIT ADTSSNTAYMQLSSLTTEDSAIY YCARWASVVVGDYWGQGATLT VSSAKTTPPSVYPLAPGSAAQTN SMVTLGCLVKGYFPEPVTVTWN SGSLSSGVHTFPAVLQSDLYTLSS SVTVPSSTWPSQTVTCNVAHPAS STKVDKKIVPRDCGCKPCICTVP EVSSVFIFPPKPKDVLTITLTPKVT CVVVDISKDDQG SEQ ID NO: 3 (IgG1) CDR1 (SEQ ID NO: 33)- GYTFTGYW CDR2 (SEQ ID NO: 34)- ILPGSTNI CDR3 (SEQ ID NO: 35) ARWASVVVGDY | MDFQVQIFSFLLISASVIMSRGQ IVLTQSPAIMSASLGERVTMTC TASSSVSSSYLHWYQQKPGSSP KLWIYSTSNLASGVPARFSGSG SGTSYSLTISSMEAEDAATYYC HQYHRSPPTFGGGTKLEIKRAD AAPTVSIFPPSSEQLTSGGASVV CFLNNFYPRDINVKWKIDGSER QNGVLNSWTDQDSKDSTYSMS STLTLTKDEYERHNSYT SEQ ID NO: 4 (kappa) CDR1 (SEQ ID NO: 36)- SSVSSSY CDR2 -STS CDR3 (SEQ ID NO: 38)- HQYHRSPPT |
| 3B1 | MKVLSLLYLLTAIPGILSDVQLQ ESGPGLVKPSQSLSLTCSVTGYSI TSAYYWNWIRQFPENKLEWMG YISHDGSNTYNPSLKNRISITRDT SKNQFFLKLNSVTTEDTATYYC ATFDSDEVYWGQGTLVTVSAA KTTPPSVYPLAPGCGDTTGSSVT LGCLVKGYFPESVTVTWNSGSL SSSVHTFPALLQSGLYTMSSSVT VPSSTWPSQTVTCSVAHPASSTT VDKKLEPSGPISTINPCPPCKECH KCPAPNLEGGPSVFIFPPKG SEQ ID NO: 5 (IgG2b) CDR1 (SEQ ID NO: 39)- YSITSAYY CDR2 (SEQ ID NO: 40)- ISHDGSN CDR3 (SEQ ID NO: 41)- ATFDSDEVY | MSVLTQVLALLLLWLTGARCD IQMTQSPASLSASVGETVTITCR ASGNIHNFLAWYQQKQGRSPQ LLVYNAKTLADGVPSRFSGSGS GAQYSLKVNSLQPEDFGNYYC QHFWSTPFTFGSGTKLEAKRAD AAPTVSIFPPSSEQLTSGGASVV CFLNNFYPRDINVKWKIDGSER QNGVLNSWTDQDSKDSTYSMS STLTLTKDEYERHNSYT SEQ ID NO: 6 (kappa) CDR1 (SEQ ID NO: 42)- GNIHNF CDR2 -NAK CDR3 (SEQ ID NO: 44)- QHFWSTPFT |
| 6A10 | MGWSWIFLLFLSGTAGVLSEVQ LQQSGPELVKPGASVKIPCKASG YTFTDYNMDWVKQSHGKSLEW IGDINPNNGGTIYNQKFKGKATL TVDKSSSTAYMELRSLTSEDTA VYYCARRGIYYGSSYAMDYWG QGTSVTVSSAKTTPPSVYPLAPG SAAQTNSMVTLGCLVKGYFPEP VTVTWNSGSLSSGVHTFPAVLQ | MESQTQVFLSLLLWVSGTCGNI MMTQSPSSLAVSAGEKVTMSC KSSQSVLYSSNQKNYLAWYQQ KPGQSPKLLIYWASTRESGVPD RFTGSGSGTDFTLTISRVQAEDL AVYYCHQYLSPYTFGGGTKLEI KRADAAPTVSIFPPSSEQLTSGG ASVVCFLNNFYPRDINVKWKID GSERQNGVLNSWTDQDSKDST |

TABLE 1-continued

| Clone | Heavy chain variable region amino acid sequence | Light chain variable region amino acid sequence |
|---|---|---|
| | SDLYTLSSSVTVPSSTWPSQTVT CNVAHPASSTKVDKKIVPRDCG CKPCICTVPEVSSVFIFPPKPKDV LTITLTPKVTCVVVDISKDDQG SEQ ID NO: 7 (IgG1) CDR1 (SEQ ID NO: 45)- GYTFTDYN CDR2 (SEQ ID NO: 46)- INPNNGGT CDR3 (SEQ ID NO: 47)- ARRGIYYGSSYAMDY | YSMSSTLTLTKDEYERHNSYT SEQ ID NO: 8 (kappa) CDR1 (SEQ ID NO: 48)- QSVLYSSNQKNY CDR2 -WAS CDR3 (SEQ ID NO: 50)- HQYLSPYT |
| 7C5 | MEWELSLIFIFALLKDVQCDVQL LETGGGLVQPGGSRGLSCEGSG FTFSGFWMSWVRQTPGKTLEWI GDINSDGTAINYAPSIKDRFTIFR DNDKSTLYLQMSNVRSEDTATY FCMRSYGSGPWCFDVWGTGTT VTVSSAKTTAPSVYPLAPVCGG TTGSSVTLGCLVKGYFPEPVTLT WNSGSLSSGVHTFPALLQSGLY TLSSSVTVTSNTWPSQTITCNVA HPASSTKVDKKIEPRVPITQNPC PPLKECPPCAAPDLLGGPSVFIFP SEQ ID NO: 9 (IgG2c) CDR1 (SEQ ID NO: 51)- GFTFSGF CDR2 (SEQ ID NO: 52)- INSDGTAI CDR3 (SEQ ID NO: 53)- MRSYGSGPWCFDV | MDFQVQIFSFLLISASVIMSRGQ IVLTQSPAIMSASLGERVTMTC TASSSVSSAYLHWYQQKPGSSP KLWIYSTSNLASGVPTRFSGSG SGTSYSLTISSMEAEDAATYYC HQYHRSPFTFGAGTKLELKRAD AAPTVSIFPPSSEQLTSGGASVV CFLNNFYPKDKGEF SEQ ID NO: 10 (kappa) CDR1 (SEQ ID NO: 54)- SSVSSAY CDR2 -STS CDR3 (SEQ ID NO: 56)- QYHRSPFT |
| 1D5 | MEWTWVFLFLLSVTAGVHSQV QLQQSGAELMKPGASVKLSCKS TDYTFTGYWIEWVKQRPGHGLE WIGEILFGSGTNNYNEKFNGKA TFTADTSSNTAYMQLSSLTTEDS AIYYCARRNNFYFDYWGQGTTL TVSSAKTTPPSVYPLAPGSAAQT NSMVTLGCLVKGYFPEPVTVTW NSGSLSSGVHTFPAVLQSDLYTL SSSVTVPSSTWPSQTVTCNVAHP ASSTKVDKKIVPRDCGCKPCICT VPEVSSVFIFPPKPKDVLTITLTP KVTCVVVDISKDDQG SEQ ID NO: 11 (IgG1) CDR1 (SEQ ID NO: 57)- DYTFTGYW CDR2 (SEQ ID NO: 58)- ILFGSGTN CDR3 (SEQ ID NO: 59)- CARRNNFYFDY | MDFQVQIFSFLLISASVIMSRGQ IVLTQSPAIMSASLGERVTMTC TASSSVSSTYLHWYQQKPGSSP KLWIYSTSNLASGVPARFSGSG SGTSYSLTITTMETEDAATYYC HQYHRSPFTFGSGTKLEIKRAD AAPTVSIFPPSSEQLTSGGASVV CFLNNFYPRDINVKWKIDSER QNGVLNSWTDQDSKDSTYSMS STLTLTKDEYERHNSYTCEATH KTSTSPR SEQ ID NO: 12 (kappa) CDR1 (SEQ ID NO: 60)- SSVSST CDR2 -STS CDR3 (SEQ ID NO: 62)- HQYHRSPFT |
| 4C8 | MEWTWVFLFLLSVTAGVHSQV QLQQSGGELMKPGASVKLSCKA TEYTFTGYWIEWIKQRPGHGLE WIGEILFGNGVTNYNENFKGKA TFTADASSNTAYMQLSSLTTEDS AIYYCARRTYFYFDYWGQGTTL TVSSAKTTPPSVYPLAPGSAAQT NSMVTLGCLVKGYFPEPVTVTW NSGSLSSGVHTFPAVLQSDLYTL SSSVTVPSSTWPSQTVTCNVAHP ASSTKVDKKIVPRDCGCKPCICT VPEVSSVFIFPPKPKDVLTITLTP KVTCVVVDISKDDQG SEQ ID NO: 13 (IgG1) CDR1 (SEQ ID NO: 63)- EYTFTGYW CDR2 (SEQ ID NO: 64)- ILFGNGVT CDR3 (SEQ ID NO: 65)- ARRTYFYFDY | MDFQVQIFSFLLISASVIMSRGQ IVLTQSPAIMSASLGERVTMTC TASSSVSSSYLHWYQQKPGSSP KLWIYSTSNLASGVPARFSGSG SGTSYSLTISSMEAEDAATYYC HQYHRSPFTFGSGTKLEIKRAD AAPTVSIFPPSSEQLTSGGASVV CFLNNFYPRDINVKWKIDSER QNGVLNSWTDQDSKDSTYSMS STLTLTKDEYERHNSYT SEQ ID NO: 14 (kappa) CDR1 (SEQ ID NO: 66)- SSVSSSY CDR2 -STS CDR3 (SEQ ID NO: 68)- HQYHRSPFT |
| 7E10 | MEWTWVFLFLLSVTAGVHSQV QLQQSGAELMKPGASVKLSCKA SGYTFTGYWIEWVKQRPGHGLE | MDFQVQIFSFLLISASVIMSRGQ IVLTQSPAIMSASLEERVTMTCT ASSSVSSSYLHWFQQKPGSSPK |

TABLE 1-continued

| Clone | Heavy chain variable region amino acid sequence | Light chain variable region amino acid sequence |
| --- | --- | --- |
| | WIGEILPGNGYTNYNEKFEGKA TFTADTSSNTAYIQLNSLTTEDS AIYYCARRGSWTMDFWGQGTS VTVSSAKTTPPSVYPLAPGSAAQ TNSMVTLGCLVKGYFPEPVTVT WNSGSLSSGVHTFPAVLQSDLY TLSSSVTVPSSTWPSQTVTCNVA HPASSTKVDKKIVPRDCGCKPCI CTVPEVSSVFIFPPKPKDVLTITL TPKVTCVVVDISKDDKG SEQ ID NO: 15 (IgG1) CDR1 (SEQ ID NO: 69)- GYTFTGYW CDR2 (SEQ ID NO: 70)- ILPGNGYT CDR3 (SEQ ID NO: 71)- ARRGSWTMDF | LWIYSTSNLASGVPARFSGSGS GTSYSLTISSMEAEDAATYYCH QYHRSPHTFGGGTKLEIKRADA APTVSIFPPSSEQLTSGGASVVC FLNNFYPRDINVKWKIDGSERQ NGVLNSWTDQDSKDSTYSMSS TLTLTKDEYERHNSYT SEQ ID NO:16 (kappa) CDR1 (SEQ ID NO: 72)- SSVSSSY CDR2 -STS CDR3 (SEQ ID NO: 74)- HQYHRSPHT |
| 9E8 | MEWIWILLFILSGTAGVQSQVQL QQSGAELARPGASVKLSCKASG YTFTSNGISWVKQTTGQGLEWI GLIYPRSGNTYYNERFKGKATL TADKSSSTAYMELRRLTSEDSA VYFCLRERETGLFDFWGQGTTL TVSSAKTTPPSVYPLAPGSAAQT NSMVTLGCLVKGYFPEPVTVTW NSGSLSSGVHTFPAVLQSDLYTL SSSVTVPSSTWPSQTVTCNVAHP ASSTKVDKKIVPRDCGCKPCICT VPEVSSVFIFPPKPKDVLTITLTP KVTCVVVDISKDDQG SEQ ID NO: 17 (IgG1) CDR1 GYTFTSNG CDR2 IYPRSGNT CDR3 LRERETGLFDF | MHFQVQIFSFLLISASVIMSRGQ IVLTQSPAIMSASPGEKVTITCS ASSSVSYMHWFQQKPGTSPKL WIYTTSNLASGVPARFSGSGSG TSYSLTISRMEAEDAATYYCQQ RSSYPPTFGGGTKLEVKRADAA PTVSIFPPSSEQLTSGGASVVCF LNNFYPRDINVKWKIDGSERQN GVLNSWTDQDSKDSTYSMSST LTLTKDEYERHNSYT SEQ ID NO: 18 (kappa) CDR1 (SEQ ID NO: 78)-SSVSY CDR2 -TTS CDR3 (SEQ ID NO: 80)- (SEQ ID NO: 75)- QQRSSYPPT (SEQ ID NO: 76)- (SEQ ID NO: 77)- |
| 3E8 | MEWTWVFLFLLSVTAGVHSQVQ LQQSGAELMKPGASVRLSCKAT GYTFTGYWIEWVKQRPGHGLEW IGEILPGSGSSNYNEKFKGKATIT ADTSSNTSDMQLNSLTTEDSAIY YCARWGHPFDYVVGLGTTLTVSS AKTTPPSVYPLAPGSAAQTNSMV TLGCLVKGYFPEPVTVTWNSGSL SSGVHTFPAVLQSDLYTLSSSVT VPSSTWPSQTVTCNVAHPASSTK VDKKIVPRDCGCKPCICTVPEVS SVFIFPPKPKDVLTITLTPKVTCV VVDISKDDQG SEQ ID NO: 19 (IgG1) CDR1 (SEQ ID NO: 81)- GYTFTGYW CDR2 (SEQ ID NO: 82)- ILPGSGSS CDR3 (SEQ ID NO: 83)- RWGHPFDY | MDFQVQIFSFLLISASVIMSRGQ IVLTQSPAIMSASLGERVTMTC TASSSVSSSYLHWYQQKPGSSP KLWIYSTSNLASGVPARFSGSG SGTSYSLTISSMEAEDAATYYC HQYHRSPRTFGGGTKLEIKRAD AAPTVSIFPPSSEQLTSGGASVV CFLNNFYPRDINVKWKIDGSER QNGVLNSWTDQDSKDSTYSMS STLTLTKDEYERHNSYT SEQ ID NO: 20 (kappa) CDR1 (SEQ ID NO: 84)- SSVSSSY CDR2 -STS CDR3 (SEQ ID NO: 86)- HQYHRSPRT |
| 5C1 | MEWTWVFLFLLSVTAGVHSQVQ LQQSGAELMKPGASVKLSCKAT DYTFTGYWIEWVKQRPGHGLEW IGQILPGSAYSNYNEKFQGKATFT ADTSSDTAFMQLSSLTAEDSAIY YCARRDYYTMDWGQGTSVTV SSAKTTAPSVYPLAPVCGGTTGS SVTLGCLVKGYFPEPVTLTWNSG | MDFQVQIFSFLLISASVIMSRGQ IVLTQSPAIMSASLGERVTMTC TASSSVSSTYLHWYQQKPGSSP KLWIYSTSNLASGVPPRFSGSG SGTSYSLTISSMEAEDAATYYC HQYHRSPFTFGSGTKLEIERAD AAPTVSIFPPSSEQLTSGGASVV CFLNNFYPRDINVKWKIDGSER |

TABLE 1-continued

| Clone | Heavy chain variable region amino acid sequence | Light chain variable region amino acid sequence |
|---|---|---|
|  | SLSSGVHTFPALLQSGLYTLSSSV<br>TVTSNTWPSQTITCNVAHPASST<br>KVDKKIEPRVPITQNPCPPLKECP<br>PCAAPDLLGGPSVFIFPPKIKDVL<br>MISLSPMVTCVVVDVSEDDQG<br>SEQ ID NO: 21 (IgG2c)<br>CDR1 (SEQ ID NO: 87)-<br>DYTFTGYW<br>CDR2 (SEQ ID NO: 88)-<br>ILPGSAYS<br>CDR3 (SEQ ID NO: 89)-<br>ARRDYYTMDY | QNGVLNSWTDQDSKDSTYSMS<br>STLTLTKDEYERHNSYT<br>SEQ ID NO: 22 (kappa)<br>CDR1 (SEQ ID NO: 90)-<br>SSVSSTY<br>CDR2 -STS<br>CDR3 (SEQ ID NO: 92)-<br>HQYHRSPFT |
| 9A1 | MEWTWVFLFLLSVTAGVHSQVQ<br>LQQSGAELMKPGASVKLSCKAT<br>GSTFTGYWIEWVKQRPGHGLEW<br>IGEILPGSGYTNYNENFKGKATIT<br>ADTSSNTAYMQLSSLTTEDSAIY<br>YCARREWYYFDYWGQTTLIVS<br>SAKTTPPSVYPLAPGSAAQTNSM<br>VTLGCLVKGYFPEPVTVTWNSG<br>SLSSGVHTFPAVLQSDLYTLSSSV<br>TVPSSTWPSQTVTCNVAHPASST<br>KVDKKIVPRDCGCKPCICTVPEV<br>SSVFIFPPKPKDVLTITLTPKVTCV<br>VVDISKDDQG<br>SEQ ID NO: 23 (IgG1)<br>CDR1 (SEQ ID NO: 93)-<br>STFTGYW<br>CDR2 (SEQ ID NO: 94)-<br>ILPGSGYT<br>CDR3 (SEQ ID NO: 95)-<br>ARREWYYFDY | MDFQVQIFSFLLISASVIMSRGQ<br>IVLTQSPAIMSASLGERVTMTC<br>TASSSVSSSYLHWYQQKPGSSP<br>KLWIYSTSNLASGVPVRFSGSG<br>SGTSYSLTISIMEAEDAATYYC<br>HQYHRSPFTFGSGTKLDIKRAD<br>AAPTVSIFPPSSEQLTSGGASVV<br>CFLNNFYPRDINVKWKIDGSER<br>QNGVLNSWTDQDSKDSTYSMS<br>STLTLTKDEYERHNSYT<br>SEQ ID NO: 24 (kappa)<br>CDR1 (SEQ ID NO: 96)-<br>SSVSSSY<br>CDR2 -STS<br>CDR3 (SEQ ID NO: 98)-<br>HQYHRSPFT |
| 1B2 | MEWTWVFLFLLSVTAGVHSQVQ<br>LQQSGAELMKPGASVKLSCKAT<br>GYTFTVYWIEWVKQRPGHGLEW<br>IGEILPGSGSINYIEKFKGKATITA<br>DTSSNTAYMQLSSLTTEDSAIYY<br>CARRTWYYFDYWGQGTTLTVSS<br>AKTTPPSVYPLAPGSAAQTNSMV<br>TLGCLVKGYFPEPVTVTWNSGSL<br>SSGVHTFPAVLQSDLYTLSSSVT<br>VPSSTWPSQTVTCNVAHPASSTK<br>VDKKIVPRDCGCKPCICTVPEVS<br>SVFIFPPKPKDVLTITLTPKVTCV<br>VVDISKDDQG<br>SEQ ID NO: 25 (IgG1)<br>CDR1 (SEQ ID NO: 99)-<br>GYTFTVYW<br>CDR2 (SEQ ID NO: 100)-<br>ILPGSGSI<br>CDR3 (SEQ ID NO; 101)-<br>ARRTWYYFDY | MDFQVQIFSFLLISASVIMSRGQ<br>IVLTQSPAIMSASLGERVTMTC<br>TASSSVSSSYLHWYQQKPGSSP<br>QLWIYSTSNLASGVPTRFSGSG<br>SGTSYSLTISSMEAEDAATYYC<br>HQYHRSPFTFGSGTKLEIKRAD<br>AAPTVSIFPPSSEQLTSGGASVV<br>CFLNNFYPRDINVKWKIDGSER<br>QNGVLNSWTDQDSKDSTYSMS<br>STLTLTKDEYERHNSYT<br>SEQ ID NO: 26 (kappa)<br>CDR1 (SEQ ID NO: 102)-<br>SSVSSSY<br>CDR2 -STS<br>CDR3 (SEQ ID NO: 104)-<br>HQYHRSPFT |

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:1 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:2.

In some embodiments, the anti-LILRB3 antibodies include a vhCDR1 comprising SEQ ID NO:27, a vhCDR2 comprising SEQ ID NO:28, a vhCDR3 comprising SEQ ID NO:29, a vlCDR1 comprising SEQ ID NO:30, a vlCDR2 comprising STS, and a vlCDR3 comprising SEQ ID NO:32. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:3 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:4.

In some embodiments, the anti-LILRB3 antibodies include a vhCDR1 comprising SEQ ID NO:33, a vhCDR2 comprising SEQ ID NO:34, a vhCDR3 comprising SEQ ID NO:35, a vlCDR1 comprising SEQ ID NO:36, a vlCDR2 comprising STS, and a vlCDR3 comprising SEQ ID NO:38. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:5 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:6.

In some embodiments, the anti-LILRB3 antibodies include a vhCDR1 comprising SEQ ID NO:39, a vhCDR2 comprising SEQ ID NO:40, a vhCDR3 comprising SEQ ID NO:41, a vlCDR1 comprising SEQ ID NO:42, a vlCDR2 comprising NAK, and a vlCDR3 comprising SEQ ID NO:44. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:7 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:8.

In some embodiments, the anti-LILRB3 antibodies include a vhCDR1 comprising SEQ ID NO:45, a vhCDR2 comprising SEQ ID NO:46, a vhCDR3 comprising SEQ ID NO:47, a vlCDR1 comprising SEQ ID NO:48, a vlCDR2 comprising WAS, and a vlCDR3 comprising SEQ ID NO:50. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:9 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:10.

In some embodiments, the anti-LILRB3 antibodies include a vhCDR1 comprising SEQ ID NO:51, a vhCDR2 comprising SEQ ID NO:52, a vhCDR3 comprising SEQ ID NO:53, a vlCDR1 comprising SEQ ID NO:54, a vlCDR2 comprising STS, and a vlCDR3 comprising SEQ ID NO:56. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:11 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:12.

In some embodiments, the anti-LILRB3 antibodies that include a vhCDR1 comprising SEQ ID NO:57, a vhCDR2 comprising SEQ ID NO:58, a vhCDR3 comprising SEQ ID NO:59, a vlCDR1 comprising SEQ ID NO:60, a vlCDR2 comprising STS, and a vlCDR3 comprising SEQ ID NO:62. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:13 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:14.

In some embodiments, the anti-LILRB3 antibodies that include a vhCDR1 comprising SEQ ID NO:63, a vhCDR2 comprising SEQ ID NO:64, a vhCDR3 comprising SEQ ID NO:65, a vlCDR1 comprising SEQ ID NO:66, a vlCDR2 comprising STS, and a vlCDR3 comprising SEQ ID NO:68. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:15 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:16.

In some embodiments, the anti-LILRB3 antibodies that include a vhCDR1 comprising SEQ ID NO:69, a vhCDR2 comprising SEQ ID NO:70, a vhCDR3 comprising SEQ ID NO:71, a vlCDR1 comprising SEQ ID NO:72, a vlCDR2 comprising STS, and a vlCDR3 comprising SEQ ID NO:74. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:17 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:18.

In some embodiments, the anti-LILRB3 antibodies include a vhCDR1 comprising SEQ ID NO:75, a vhCDR2 comprising SEQ ID NO:76, a vhCDR3 comprising SEQ ID NO:77, a vlCDR1 comprising SEQ ID NO:78, a vlCDR2 comprising TTS, and a vlCDR3 comprising SEQ ID NO:80. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:19 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:20.

In some embodiments, the anti-LILRB3 antibodies include a vhCDR1 comprising SEQ ID NO:81, a vhCDR2 comprising SEQ ID NO:82, a vhCDR3 comprising SEQ ID NO:83, a vlCDR1 comprising SEQ ID NO:84, a vlCDR2 comprising STS, and a vlCDR3 comprising SEQ ID NO:86. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:21 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:22.

In some embodiments, the anti-LILRB3 antibodies include a vhCDR1 comprising SEQ ID NO:87, a vhCDR2 comprising SEQ ID NO:88, a vhCDR3 comprising SEQ ID NO:89, a vlCDR1 comprising SEQ ID NO:90, a vlCDR2 comprising STS, and a vlCDR3 comprising SEQ ID NO:92. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:23 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:24.

In some embodiments, the anti-LILRB3 antibodies include a vhCDR1 comprising SEQ ID NO:93, a vhCDR2 comprising SEQ ID NO:94, a vhCDR3 comprising SEQ ID NO:95, a vlCDR1 comprising SEQ ID NO:96, a vlCDR2 comprising STS, and a vlCDR3 comprising SEQ ID NO:98. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In some embodiments, the anti-LILRB3 antibodies in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:25 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:26.

In some embodiments, the anti-LILRB3 antibodies include a vhCDR1 comprising SEQ ID NO:99, a vhCDR2 comprising SEQ ID NO:100, a vhCDR3 comprising SEQ ID NO:101, a vlCDR1 comprising SEQ ID NO:102, a vlCDR2 comprising STS, and a vlCDR3 comprising SEQ ID NO:104. In some embodiments, one or more of such 6 CDRs have from 1, 2, 3, 4 or 5 amino acid modifications. In further embodiments, a single CDR contains 1 or 2 amino acid substitutions, and the modified anti-LILRB3 antibodies retain binding to human LILRB3.

In addition to the sequence variants described herein in the heavy chain and light chain variable regions and/or CDRs, changes in the framework region(s) of the heavy and/or light variable region(s) can be made. In some embodiments, variants in the framework regions (e.g., excluding the CDRs) retain at least about 80, 85, 90 or 95% identity to a germline sequence. Variants can be made to retain at least about 80, 85, 90 or 95% identity to any one of the light chain V-GENE, light chain J-GENE, heavy chain V-GENE, heavy chain J-GENE, and heavy chain D-GENE alleles.

In some embodiments, variations are made in the framework regions that retain at least 80, 85, 90 or 95% identity to the germline gene sequences, while keeping 6 CDRs unchanged.

In some embodiments, variations are made in both the framework regions that retain at least 80, 85, 90 or 95% identity to germline gene sequences. The CDRs can have amino acid modifications (e.g., from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g., there may be one change in vlCDR1, two in vhCDR2, none in vhCDR3, etc.).

By selecting amino acid sequences of CDRs and/or variable regions of a heavy chain and a light chain from those described herein and combining them with amino acid sequences of framework regions and/or constant regions of a heavy chain and a light chain of an antibody as appropriate, a person skilled in the art will be able to design an anti-LILRB3 antibody according to the present invention. The antibody framework regions and/or constant region (Fc domain) described in the current invention can derive from an antibody of any species, such as from human, rabbit, dog, cat, mouse, horse or monkey.

In some embodiments, the constant region is derived from human, and includes a heavy chain constant region derived from those of IgG, IgA, IgM, IgE, and IgD subtypes or variants thereof, and a light chain constant region derived from kappa or lambda subtypes or variants thereof. In some embodiments, the heavy chain constant region is derived from a human IgG, including IgG1, IgG2, IgG3, and IgG4. In some embodiments, the amino acid sequence of the heavy chain constant region is at least 80%, 85%, 90%, or 95% identical to a human IgG1, IgG2, IgG3, or IgG4 constant region. In some other embodiments, the amino acid sequence of the constant region is at least 80%, 85%, 90%, or 95% identical to an antibody constant region from another mammal, such as rabbit, dog, cat, mouse, horse or monkey. In some embodiments, the antibody constant region includes a hinge, a CH2 domain, a CH3 domain and optionally a CH1 domain.

In some embodiments, the antibodies described herein can be derived from a mixture from different species, e.g., forming a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system, as described for example in Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al.,1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci, USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. Other humanization methods may involve the grafting of only parts of the CDRs, including but not limited to methods described in Tan et al., 2002, J. Immunol. 169:1119-1125; De Pascalis et al., 2002, J. Immunol. 169:3076-3084, all entirely incorporated by reference.

In some embodiments, the antibodies of the current invention comprise a heavy chain variable region derived from a particular human germline heavy chain immunoglobulin gene and/or a light chain variable region derived from a particular human germline light chain immunoglobulin gene. Such antibodies may contain amino acid differences as compared to the human germline sequences, due to, for example, naturally-occurring somatic mutations or intentional introduction of site-directed mutation. However, a humanized antibody typically is at least 80% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the human germline immunoglobulin gene. Typically, a humanized antibody derived from a particular human germline sequence will display no more than 10-20 amino acid differences from the amino acid sequence encoded by the human germline immunoglobulin gene. In certain cases, the humanized antibody may display no more than 5, or even no more than 4, 3, 2, or 1 amino acid difference from the amino acid sequence encoded by the germline immunoglobulin gene.

In some embodiments, the antibodies of the current disclosure are humanized and affinity matured, as is known in the art. Structure-based methods may be employed for humanization and affinity maturation, for example as described in U.S. Pat. No. 7,657,380. Selection based methods may be employed to humanize and/or affinity mature antibody variable regions, including but not limited to methods described in Wu et al., 1999, J. Mol. Biol. 294: 151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10): 753-759, all entirely incorporated by reference.

II. Characteristics of the Antibodies

In some embodiments, the anti-LILRB3 antibodies described herein bind to human LILRB3. In some embodiments, binding of the anti-LILBR3 antibodies to human LILRB3 is measured by Flow cytometry, such as the exemplary assay described in Example 1.

In some embodiments, the anti-LILRB3 antibodies display low immunogenicity when administered into human subjects. These antibodies can contain an Fc domain derived from human IgG1, human IgG2 or human IgG3. In some embodiments, these antibodies are humanized using the framework regions derived from human immunoglobulins.

In some embodiments, the anti-LILRB3 antibodies affect the responsiveness of T cells. In some embodiments the anti-LILRB3 antibodies regulate surface expression of activation markers in response to different types of T cell stimulation, such as the exemplary assay described in Example 3. In some embodiments the anti-LILRB3 antibodies regulate cytokine production by PBMCs in response to T cell stimulation, such as the exemplary assay described in Example 4.

In some embodiments, anti-LILRB3 antibodies described act as LILRB3 antagonists. As a result, such anti-LILRB3 antibodies inhibit the activity of LILRB3.

In some other embodiments, anti-LIRB3 antibodies described herein act as LILRB3 agonists. As a result, such anti-LILRB3 antibodies promote the activity of LILRB3.

Effects of the anti-LILRB3 antibodies on T cell function can be assayed using a variety of methods known in the art and described herein. Accordingly, the anti-LILRB3 antibodies can serve as LILRB3 antagonists or LILRB3 agonists.

III. Nucleic Acids of the Invention

Nucleic acids encoding the anti-LILRB3 antibodies described herein are also encompassed by the present disclosure, as well as expression vectors containing such nucleic acids and host cells transformed with such nucleic acids and/or expression vectors. As will be appreciated by those in the art, the protein sequences depicted herein can be encoded by any number of possible nucleic acid sequences due to the degeneracy of the genetic code, and one of skill in the art could readily identify such nucleic acid sequences based on the amino acid sequences provided herein.

In some embodiments, nucleic acid compositions encoding the anti-LILRB3 antibodies and/or LILRB3-binding domains are also encompassed by the invention. As will be appreciated by those in the art, in the case of antigen binding domains, the nucleic acid compositions generally include a first nucleic acid encoding the heavy chain variable region and a second nucleic acid encoding the light chain variable region. In the case of scFvs, a single nucleic acid encoding the heavy chain variable region and light chain variable region, separated by a linker described herein, can be made. In the case of traditional antibodies, the nucleic acid compositions generally include a first nucleic acid encoding the heavy chain and a second nucleic acid encoding the light chain, which will, upon expression in a cell, spontaneously assemble into the "traditional" tetrameric format of two heavy chains and two light chains.

In some embodiments, the nucleic acid compositions encoding the anti-LILRB3 antibodies and/or LILRB3-binding domains are codon optimized versions or variants.

As is known in the art, the nucleic acids encoding the components of the invention can be incorporated into expression vectors, and depending on the host cells, used to produce the antibodies of the invention. These two nucleic acids can be incorporated into a single expression vector or into two different expression vectors. Generally, the nucleic acids can be operably linked to any number of regulatory elements (promoters, origin of replication, selectable markers, ribosomal binding sites, inducers, etc.) in an expression vector. The expression vectors can be extra-chromosomal or integrating vectors.

The nucleic acids and/or expression vectors of the current invention can be introduced into any type of host cells, which are well known in the art, including mammalian, bacterial, yeast, insect and fungal cells. After transfection, single cell clones can be isolated for cell bank generation using methods known in the art, such as limited dilution, ELISA, FACS, microscopy, or Clonepix. Clones can be cultured under conditions suitable for bio-reactor scale-up and maintained expression of the antibodies. The antibodies can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

IV. Therapeutic Applications

The current disclosure provides a method of modulating an immune response in a subject, and the method includes administering to the subject an effective amount of an anti-LILRB3 antibody described herein, or a pharmaceutical composition containing an anti-LILRB3 antibody.

In some embodiments, the methods of modulating an immune response encompassed by the present disclosure comprises inhibiting LILRB3 activity in a subject, and in further embodiments, such methods comprise administering to the subject an effective amount of an anti-LILRB3 antibody that acts as a LILRB3 antagonist, or by administering a pharmaceutical composition containing an antagonistic anti-LILRB3 antibody.

In some embodiments, the methods of modulating an immune response encompassed by the present disclosure comprises promoting LILRB3 activity in a subject, and in further embodiments, such methods comprise administering to the subject an effective amount of an anti-LILRB3 antibody that acts as a LILRB3 agonist, or by administering a pharmaceutical composition containing an agonistic anti-LILRB3 antibody.

In some embodiments, an antagonist may stimulate and immune response. In other embodiments an antagonistic may inhibit an immune response. In some embodiments an agonist may stimulate an immune response. In other embodiments an agonist may inhibit an immune response.

The present disclosure also provides methods of treating cancer in a subject, and such methods include administering to the subject an effective amount of an anti-LILRB3 antibody, or a pharmaceutical composition containing such anti-LILRB3 antibody. In some embodiments, the cancer to be treated expresses LILRB3 on the cancer cell surface. In some embodiments, the cancer to be treated upregulates LILRB3 compared to the corresponding non-cancerous tissue. In some embodiments, the subject to be treated expresses LILRB3 on one or more types of immune cells including lymphoid cells, myeloid cells, monocytes, monocyte-derived osteoclasts, granulocytes, dendritic cells, osteoclasts, and progenitor mast cells. In some embodiments, the subject to be treated expresses a high level of LILRB3 on one or more types of immune cells including monocytes, monocyte-derived osteoclasts, granulocytes, dendritic cells, osteoclasts, and progenitor mast cells. In some embodiments, the subject to be treated expresses a high level of LILRB3 on hematopoietic cancer cells. In some embodiments, the cancer to treated is non-responsive to existing immune-modulating antibodies targeting other immune checkpoints, such as CTLA-4, PD-1 or PD-L1.

In some embodiments, the cancer is myeloid leukemia, B lymphoid leukemia, or myeloma.

In some other embodiments, the cancer is brain cancer, bladder cancer, breast cancer, cervical cancer, endometrial cancer, esophageal cancer, leukemia, lung cancer, liver cancer, melanoma, ovarian cancer, pancreatic cancer, prostate cancer, rectal cancer, renal cancer, testicular cancer, or uterine cancer. In yet other embodiments, the cancer is a vascularized tumor, squamous cell carcinoma, adenocarcinoma, small cell carcinoma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VlPoma, vulva cancer, well-differentiated carcinoma, or Wilms tumor.

In some other embodiments, the cancer to be treated is a non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

The present disclosure also provides methods of treating autoimmune or inflammatory disorders in a subject, and the method includes administering to the subject an effective amount of an anti-LILRB3 antibody that acts as a modulator of LILRB3. In some embodiments, the subject to be treated expresses LILRB3 on one or more types of immune cells including lymphoid cells, myeloid cells, monocytes, monocyte-derived osteoclasts, granulocytes, dendritic cells, osteoclasts, and progenitor mast cells. In some embodiments, the subject to be treated expresses a high level of LILRB3 on one or more types of immune cells including lymphoid cells, myeloid cells, monocytes, monocyte-derived osteoclasts, granulocytes, dendritic cells, osteoclasts, and progenitor mast cells. In some embodiments, LILRB3 is expressed in the subject at a high level on autoreactive immune cells (e.g., T cells, B cells, natural killer cells, dendritic cells, endothelial cells, and macrophages at sites where the autoimmune disease develops, for example, lymph nodes and central nervous system in the subject suffering from multiple sclerosis, joints in the subject suffering from Rheumatoid arthritis, and gastrointestinal tract in the subject suffering from Celiac disease). Administering an anti-LILRB3 antibody that acts as a LILRB3 antagonist can inhibit LILRB3 activity. Administering an anti-LILRB3 antibody that acts as a LILRB3 agonist can promote LILRB3 activity.

In some embodiments, the autoimmune or inflammatory disorder to treated is asthma, multiple sclerosis, Addison's disease, amyotrophic lateral sclerosis, Crohn's disease, Cushing's Syndrome, diabetes mellitus type 1, graft versus host disease, Graves' disease, Guillain-Barré syndrome, lupus erythematosus, psoriasis, psoriatic arthritis, rheumatoid arthritis, sarcoidosis, scleroderma, systemic lupus erythematosus, transplant rejection, or vasculitis.

In some other embodiments, the autoimmune disorders to be treated include, but are not limited to, Acute disseminated encephalomyelitis (ADEM), Agammaglobulinemia, Alopecia areata, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behcet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Cutaneous leukocytoclastic angiitis, Dego's disease, Dercum's disease, Dermatitis herpetiformis, Dermatomyositis, Diffuse cutaneous systemic sclerosis, Discoid lupus erythematosus, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease, Lupoid hepatitis aka Autoimmune hepatitis, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Ménière's disease, Narcolepsy, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Pars planitis, Parsonage-Turner syndrome, Pemphigus vulgaris, Perivenous encephalomyelitis, Pernicious anaemia, POEMS syndrome, Polyarteritis nodosa, Polymyalgia rheumatica, Polymyositis, Primary biliary cirrhosis, Primary sclerosing cholangitis, Progressive inflammatory neuropathy, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Schizophrenia, Schmidt syndrome, Schnitzler syndrome, Scleritis, Serum Sickness, Sjögren's syndrome, Spondyloarthropathy, Stiff person syndrome, Still's disease, Subacute bacterial endocarditis (SBE), Susac's syndrome, Sweet's syndrome, Sydenham chorea, Sympathetic ophthalmia, Takayasu's arteritis, Temporal arteritis, Thrombocytopenia, Tolosa-Hunt syndrome, Transverse myelitis, Ulcerative colitis, Undifferentiated spondyloarthropathy, Urticarial vasculitis, Vitiligo, Wegener's granulomatosis.

The present disclosure also provides methods of treating allergic inflammation in a subject, and the method includes administering to the subject an effective amount of any one of the anti-LILRB3 antibodies described herein, or any one of the compositions described herein.

In some embodiments, the allergic inflammation to be treated may be related to allergic asthma, atopic dermatitis, allergic rhinitis, allergic conjunctivitis.

The present disclosure also provides methods of modulating osteoclast differentiation, and the method includes administering to the subject an effective amount of any one of the anti-LILRB3 antibodies described herein, or any one of the compositions described herein.

In some embodiments, modulating osteoclast differentiation may be particularly useful to treat bone loss or bone resorption in patients suffering or susceptible of suffering from a condition selected from the group consisting of osteoporosis, osteodystrophy, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets) or other form of vitamin D deficiency such as vitamin D deficiency associated with chronic kidney disease or kidney failure, fibrogenesis imperfecta ossium, osteosclerotic disorders such as pycnodysostosis and damage caused by macrophage-mediated inflammatory processes.

V. Combination Therapy

Anti-LILRB3 antibodies described herein can be used in combination with additional therapeutic agents to treat cancer, autoimmune disorders, and allergic inflammation. Anti-LILRB3 antibodies can also be used in combination with additional therapeutic agents to modulate osteoclast differentiation Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAG3, (v) B7-H3, (vi) B7-H4, and (vii) TIM3, such as Ipilimumab, Nivolumab, Pembrolizumab, Avelumab, Durvalumab, and Atezolizumab.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF. Antibodies of the invention can also be used as an adjunct to surgical removal of cancer from the primary lesion.

Exemplary therapeutic agents that may be used as a part of a combination therapy with the anti-LILRB3 antibodies for treating, delaying the progression of, preventing a relapse of, or alleviating a symptom of an autoimmune or inflammatory disorder, include, for example, any of a variety of known anti-inflammatory and/or immunosuppressive therapy. In some embodiments, the anti-inflammatory and/or immunosuppressive therapies include, but are not limited to methotrexate, cyclosporin A (including, for example, cyclosporin microemulsion), tacrolimus, corticosteroids, statins, interferon beta, non-steroidal anti-inflammatory agents, and 6-MP (Mercaptopurine, also called 6-Mercaptopurine, or Purinethol).

In some embodiments, the anti-inflammatory and/or immunosuppressive therapies for combining with the anti-LILRB3 antibodies include, but are not limited to a TOPK inhibitor (e.g., OTS964 ((R)-9-(4-(1-(dimethylamino)propan-2-yl)phenyl)-8-hydroxy-6-methylthieno[2,3-c] quinolin-4(5H)-one) (Oncotherapy Science)), a tyrosine kinase inhibitor (e.g., axitinib, dasatinib, icotinib), a topoisomerase inhibitor (e.g., topotecan), a sphingosine-1-phosphate receptor agonist (e.g., fingolimod, KRP-203), anti-T cell immunoglobulin (e.g. AtGam), anti-IL-2 receptor antibody (e.g. daclizumab), amides (CTX), ifosfamide (IFO), adriamycin (ADM), daunorubicin (DNR), vincristine (VCR), vinblastine (VBL), etoposide (VP16), vermeer (Vumon), carboplatin (CBP), tacrolimus, sirolimus, everolimus, azathioprine, brequinar, leflunomide, LEA-29Y, anti-CD3 antibody (e.g. OKT3), aspirin, B7-CD28 blocking molecules (e.g. belatacept, abatacept), CD40-CD154 blocking molecules (anti-CD40 antibodies), acetaminophen, ibuprofen, naproxen, piroxicam, and anti-inflammatory steroids (e.g. prednisolone or dexamethasone).

In some embodiments, the anti-inflammatory and/or immunosuppressive therapies for combining with the anti-LILRB3 antibodies include ablation of autoimmune cells, for example, by administration of TNF-alpha, CFA, interleukin-1 (IL-1), proteasome inhibitors, NFκB inhibitors, anti-inflammatory drugs, tissue plasminogen activator (TPA), lipopolysaccharide, UV light, and an intracellular mediator of the TNF-alpha signaling pathway. Such agents induce the apoptosis of autoreactive lymphocytes by interrupting the pathway downstream from TNF-alpha receptor signaling or act downstream of TNF-alpha receptor binding. (Baldwin et al., Ann. Rev. Immunol.(1996) 12:141; Baltimore, Cell (1996) 87:13).

In some embodiments, the anti-LILRB3 antibodies are used in conjunction with a surgical method of treating or otherwise alleviating autoimmune diseases.

Exemplary therapeutic agents that may be used as a part of a combination therapy with the anti-LILRB3 antibodies for treating, delaying the progression of, preventing a relapse of, or alleviating a symptom of allergic inflammation, include, for example, any of a variety of known anti-inflammatory and/or immunosuppressive therapies. In some embodiments, the anti-inflammatory and/or immunosuppressive therapies for combining with anti-LILRB3 antibodies include but are not limited to: short-acting β2-agonists, long-acting β2-agonists, anticholinergics, corticosteroids, systemic corticosteroids, mast cell stabilizers, leukotriene modifiers, methylxanthines, β32-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methyprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; and combinations thereof.

In other embodiments, therapeutic agents that may be used as a part of a combination therapy with the anti-LILRB3 antibodies for treating, delaying the progression of, preventing a relapse of, or alleviating a symptom of allergic inflammation, may also include those therapeutic agents specified for autoimmune or inflammatory disorders.

Exemplary therapeutic agents that may be used as a part of a combination therapy with the anti-LILRB3 antibodies for modulating osteoclast activity include but are not limited to bisphosphonates, calcitonin, estrogen replacement, sclerostin antibodies, RANKL antibodies, parathyroid peptides, strontiumranelate, TNFα inhibitors, colony-stimulating factor-1 inhibitors, colony-stimulating factor-1 receptor inhibitors, cathepsin K inhibitors, V-ATPase inhibitors, and Glucagon-like peptide 2.

The amount of the antibodies and additional therapeutic agents and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

VI. Pharmaceutical Composition and Administration

The present disclosure also features pharmaceutical compositions/formulations that contain a therapeutically effective amount of an anti-LILRB3 antibody described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The antibodies of the present disclosure can exist in a lyophilized formulation or liquid aqueous pharmaceutical formulation. The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

The antibodies of the present disclosure could exist in a lyophilized formulation including the proteins and a lyoprotectant. The lyoprotectant may be sugar, e.g., disaccharides. In certain embodiments, the lyoprotectant is sucrose or maltose. The lyophilized formulation may also include one or more of a buffering agent, a surfactant, a bulking agent, and/or a preservative.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. It may be administered in the range of 0.1 mg to 1 g and preferably in the range of 0.5 mg to 500 mg of active antibody per administration for adults. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., Clinica Chimica Acta 308: 43-53, 2001; Steimer et al., Clinica Chimica Acta 308: 33-41, 2001).

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

EXAMPLES

The invention now being generally described, will be more readily understood by reference to the following examples, which are included merely for purposes of illustration of certain aspects and embodiments of the present invention, and is not intended to limit the invention.

Example 1

LILRB3 Surface Expression on Hematopoietic Cell Subsets

Figure 1B:
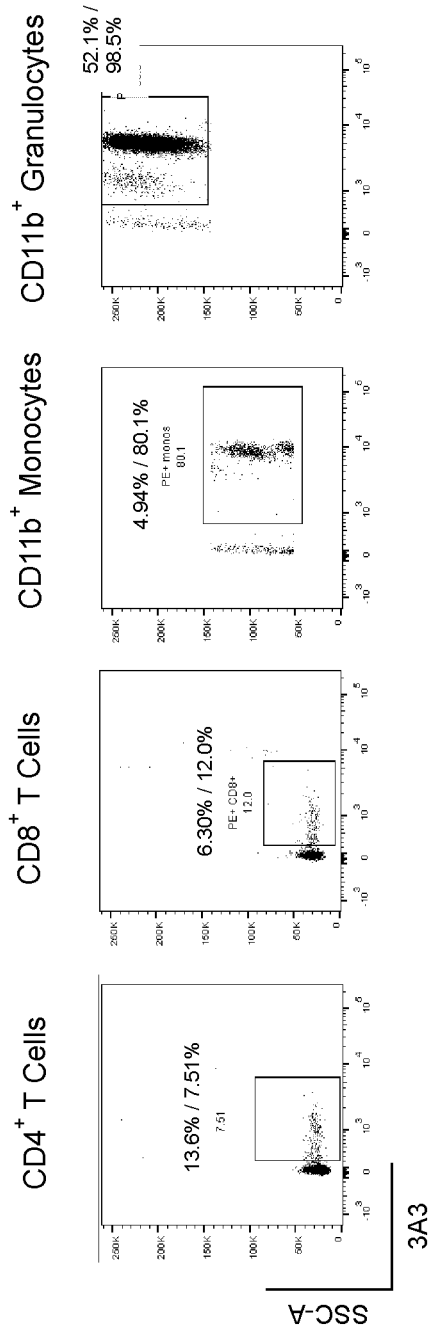
Figure 2:
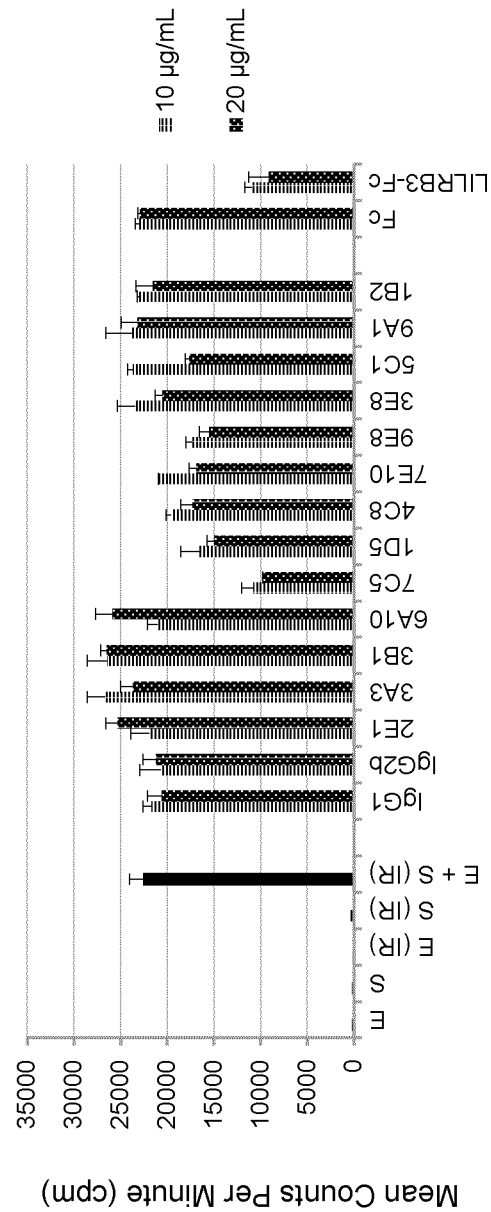
FIG. 2 shows the effect of LILRB3 antibodies or LILRB3-Fc protein on responsiveness of T cells in primary mixed lymphocyte reactions (MLR).

LILRB3 surface expression was measured on various hematopoietic subsets in the form of two-dimensional flow cytometry (FCM) representations called quantile contour plots (probability plots). Peripheral blood mononuclear cells (PBMCs) from a healthy human donor were stained with the LILRB3 3A3 antibody as well as antibodies specific for the indicated cell subset. FIG. 1A plots depict LILRB3 expression by gated CD3+CD4+ T cells, CD3+CD8+ T cells or CD11b+ monocytes. In FIG. 1B, fresh whole blood from a healthy human donor was stained as in FIG. 1A. Plots depict LILRB3 expression by gated CD3+CD4+ T cells, CD3+CD8+ T cells, CD11b+ monocytes or CD11b+ granulocytes. Percentages of gated cells and of LILRB3+ cells within the gated population are depicted inside the plots (first and second numbers, respectively). LILRB3 expression is demonstrated on monocytes and granulocytes, and low LILRB3 expression is demonstrated on CD4+ or CD8+ T cells. Specificity of the LILRB3 staining was determined by staining all of the above cell subsets with an IgG1 isotype control antibody. Data are representative of several independent experiments utilizing different human blood samples.

Example 2

The Effect of LILRB3 Antibodies or LILRB3-Fc Protein on T Cell Responsiveness in Primary Mixed Lymphocyte Reactions (MLR)

CD3+ T cells [$1\times10^5$ cells, effector (E) population] and irradiated (IR) allogenic CD14+ monocytes [$2\times10^5$ cells, stimulator (S) population] from healthy human donors were co-cultured in the presence or absence of the indicated amounts of IgG1 or IgG2b isotype control antibodies, LILRB3 antibodies, Fc protein or Fc-LILRB3 protein. After 3 days, the cells were labeled with 3H-thymidine for an additional 18 hours to measure T cell proliferation. The LILRB3 7C5 antibody and LILRB3 Fc proteins inhibited T cell proliferation (Fi 2). Data shown are representative of several independent experiments utilizing different effector/stimulator pairs, and are reported as the mean counts per minute (cpm)±standard error of triplicate wells.

Example 3

Figure 3A:
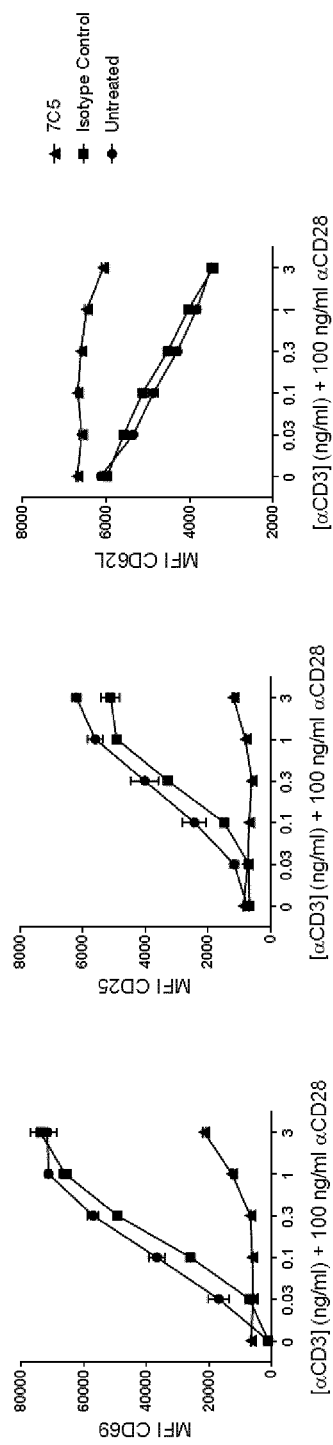
FIG. 3 shows the ability of PBMCs to regulate surface expression of activation markers in response to T cell stimulation after incubation with the LILRB3 7C5 antibody.
Figure 3B:
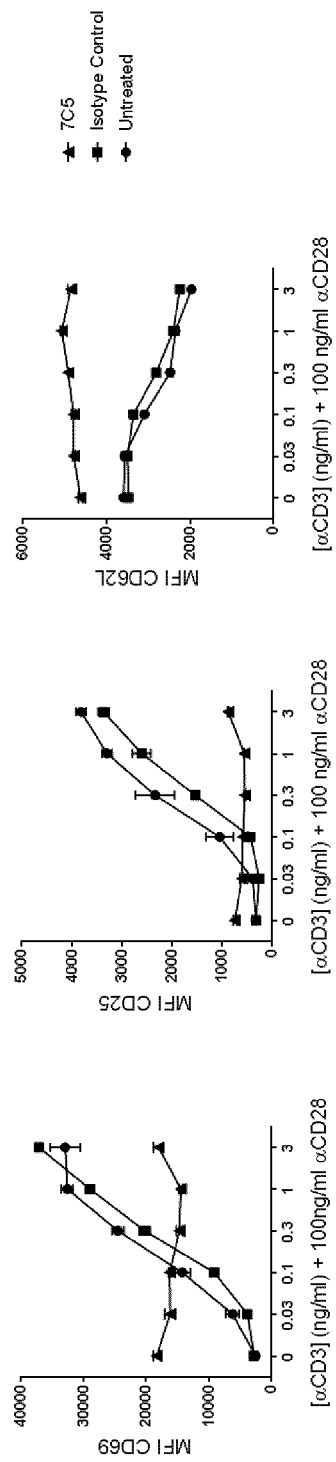

PBMC Incubated with LILRB3 7C5 Antibody are Unable to Fully Regulate the Surface Expression of Activation Markers in Response to T Cell Stimulation PBMCs ($2\times10^5$ cells) from a healthy human donor were cultured in the presence or absence of 7C5 or isotype control antibody (20 μg/mL) and the indicated amounts of anti-CD3 and anti-CD28 antibodies. After 24 hours, the cells were stained with antibodies specific for the indicated cell subset and activation markers. In Panel A, plots depict CD69, CD25 and CD62L expression by gated CD3+CD4+ T cells (FIG. 3A). In Panel B, plots depict CD69, CD25 and CD62L expression by gated CD3+CD8+ T cells (FIG. 3B). The LILRB3 7C5 antibody inhibits the activation of CD4+ and CD8+ T cells by anti-CD3 and anti-CD28 antibodies as shown by reduced expression of CD69 (type II C-lectin receptor) and CD25 (IL-2 receptor), and reduced shedding of CD62L (L-selectin). Data are representative of several independent experiments utilizing different human PBMC samples, and are reported as the mean fluorescence intensity (MFI)±standard error of triplicate wells.

Example 4

Figure 4:
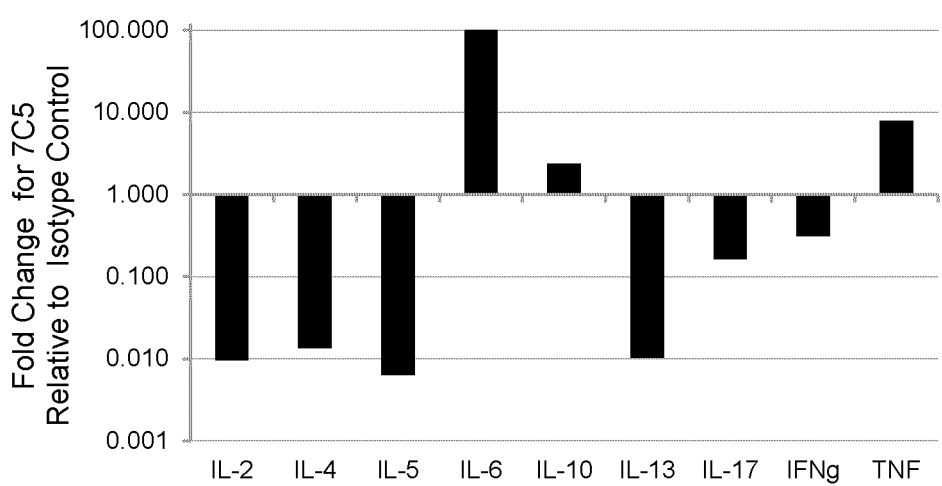
FIG. 4 shows the effect of the LILRB3 7C5 antibody on cytokine production by PBMCs in response to T cell stimulation.

LILRB3 Antibodies Alter Cytokine Production by PBMC in Response to T Cell Stimulation PBMCs ($2\times10^5$ cells) from a healthy human donor were cultured in the presence or absence of 7C5 or isotype control antibody (20 μg/mL), and anti-CD3 (1 ng/mL) and anti-CD28 (100 ng/mL) antibodies. After 24 hours, cytokine levels in culture supernatants were determined by a BioLegend LEGENDplex Human Th Cytokine Panel by manufacturer's instructions. In the presence of 7C5, the level of certain cytokines, including IL-2, IL-4, IL-5, IL-13, IL-17 and IFNγ were decreased, while the level IL-6, IL-10 and TNF were increased (FIG. 4). Data are representative of several independent experiments utilizing different human PBMC samples, and are reported as the fold change for 7C5 relative to the isotype control antibody of duplicate wells.

Example 5

Figure 5:
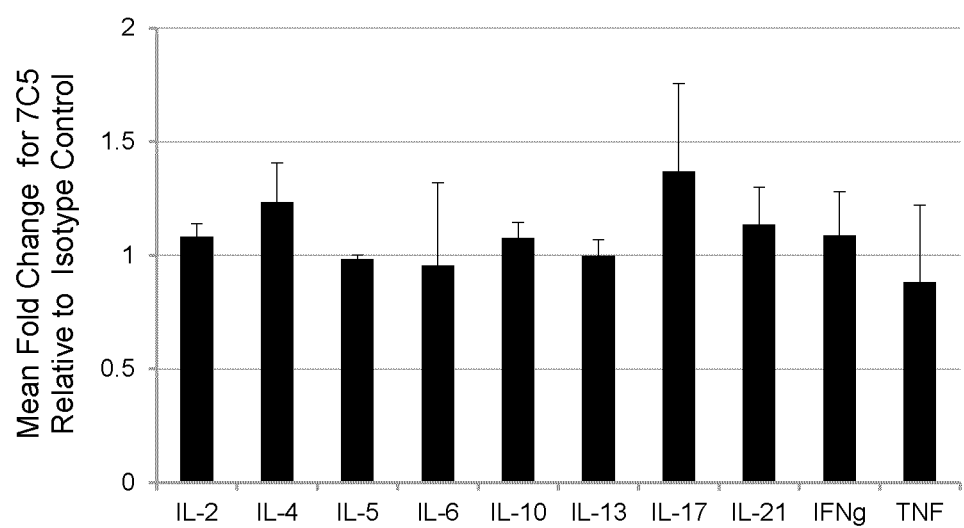
FIG. 5 shows cytokine release of unstimulated blood when incubated with the LILRB3 7C5 antibody.

LILRB3 7C5 Antibody Causes No Significant Release of Cytokines from Unstimulated Whole Blood Fresh blood from healthy human donors (n=4) was diluted 4:1 with RPMI 1640 medium and cultured for 4 hours in the presence of 7C5 or isotype control antibody (50 µg/mL). LPS (1 µg/mL) was used as a positive control. Cytokine levels in serum samples were determined by a BioLegend LEGENDplex Human Th Cytokine Panel by manufacturer's instructions. The LILRB3 7C5 antibody showed no significant stimulatory effect in the absence of a T cell receptor stimulus (FIG. 5). Data are representative of several independent experiments, and are reported as the mean fold change for 7C5 relative to the isotype control antibody of duplicate wells.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. An antibody that binds to human LILRB3, the antibody comprising a heavy chain variable region comprising a vhCDR1, a vhCDR2, and a vhCDR3 and a light chain variable region comprising a vlCDR1, a vlCDR2, and a vlCDR3, wherein the vhCDR1, vhCDR2, vhCDR3, vlCDR1, vlCDR2 and vlCDR3 are selected from the following:
   a) a vhCDR1 comprising SEQ ID NO:51, a vhCDR2 comprising SEQ ID NO:52, a vhCDR3 comprising SEQ ID NO:53, a vlCDR1 comprising SEQ ID NO:54, a vlCDR2 comprising STS, and a vlCDR3 comprising SEQ ID NO:56;
   b) a vhCDR1 comprising SEQ ID NO:33, a vhCDR2 comprising SEQ ID NO:34, a vhCDR3 comprising SEQ ID NO:35, a vlCDR1 comprising SEQ ID NO:36, a vlCDR2 comprising STS, and a vlCDR3 comprising SEQ ID NO:38;
   c) a vhCDR1 comprising SEQ ID NO:39, a vhCDR2 comprising SEQ ID NO:40, a vhCDR3 comprising SEQ ID NO:41, a vlCDR1 comprising SEQ ID NO:42, a vlCDR2 comprising NAK, and a vlCDR3 comprising SEQ ID NO:44;
   d) a vhCDR1 comprising SEQ ID NO:45, a vhCDR2 comprising SEQ ID NO:46, a vhCDR3 comprising SEQ ID NO:47, a vlCDR1 comprising SEQ ID NO:48, a vlCDR2 comprising WAS, and a vlCDR3 comprising SEQ ID NO:50;
   e) a vhCDR1 comprising SEQ ID NO:27, a vhCDR2 comprising SEQ ID NO:28, avhCDR3 comprising SEQ ID NO:29, a vlCDR1 comprising SEQ ID NO:30, a vlCDR2 comprising STS, and a vlCDR3 comprising SEQ ID NO:32;
   f) a vhCDR1 comprising SEQ ID NO:57, a vhCDR2 comprising SEQ ID NO:58, a vhCDR3 comprising SEQ ID NO:59, a vlCDR1 comprising SEQ ID NO:60, a vlCDR2 comprising STS, and a vlCDR3 comprising SEQ ID NO:62;
   g) a vhCDR1 comprising SEQ ID NO:63, a vhCDR2 comprising SEQ ID NO:64, a vhCDR3 comprising SEQ ID NO:65, a vlCDR1 comprising SEQ ID NO:66, a vlCDR2 comprising STS, and a vlCDR3 comprising SEQ ID NO:68;
   h) a vhCDR1 comprising SEQ ID NO:69, a vhCDR2 comprising SEQ ID NO:70, a vhCDR3 comprising SEQ ID NO:71, a vlCDR1 comprising SEQ ID NO:72, a vlCDR2 comprising STS, and a vlCDR3 comprising SEQ ID NO:74;
   i) a vhCDR1 comprising SEQ ID NO:75, a vhCDR2 comprising SEQ ID NO:76, a vhCDR3 comprising SEQ ID NO:77, a vlCDR1 comprising SEQ ID NO:78, a vlCDR2 comprising TTS, and a vlCDR3 comprising SEQ ID NO:80;
   j) a vhCDR1 comprising SEQ ID NO:81, a vhCDR2 comprising SEQ ID NO:82, a vhCDR3 comprising SEQ ID NO:83, a vlCDR1 comprising SEQ ID NO:84, a vlCDR2 comprising STS, and a vlCDR3 comprising SEQ ID NO:86;
   k) a vhCDR1 comprising SEQ ID NO:87, a vhCDR2 comprising SEQ ID NO:88, a vhCDR3 comprising SEQ ID NO:89, a vlCDR1 comprising SEQ ID NO:90, a vlCDR2 comprising STS, and a vlCDR3 comprising SEQ ID NO:92;
   l) a vhCDR1 comprising SEQ ID NO:93, a vhCDR2 comprising SEQ ID NO:94, a vhCDR3 comprising SEQ ID NO:95, a vlCDR1 comprising SEQ ID NO:96, a vlCDR2 comprising STS, and a vlCDR3 comprising SEQ ID NO:98; or
   m) a vhCDR1 comprising SEQ ID NO:99, a vhCDR2 comprising SEQ TD NO: 100, a vhCDR3 comprising SEQ ID NO:101, a vlCDR1 comprising SEQ ID NO:102, a vlCDR2 comprising STS, and a vlCDR3 comprising SEQ ID NO:104.

2. The antibody according to claim 1, the antibody comprising:
   a) a heavy chain variable region comprised in amino acid sequence of SEQ ID NO:9 and a light chain variable region comprised in amino acid sequence of SEQ ID NO:10;
   b) a heavy chain variable region comprised in amino acid sequence of SEQ ID NO:3 and a light chain variable region comprised in amino acid sequence of SEQ ID NO:4;
   c) a heavy chain variable region comprised in amino acid sequence of SEQ ID NO:5 and a light chain variable region comprised in amino acid sequence of SEQ ID NO:6;
   d) a heavy chain variable region comprised in amino acid sequence of SEQ ID NO:7 and a light chain variable region comprised in amino acid sequence of SEQ ID NO:8;

e) a heavy chain variable region comprised in amino acid sequence of SEQ ID NO:1 and a light chain variable region comprised in amino acid sequence of SEQ ID NO:2;
f) a heavy chain variable region comprised in amino acid sequence of SEQ ID NO:11 and a light chain variable region comprised in amino acid sequence of SEQ ID NO:12;
g) a heavy chain variable region comprised in amino acid sequence of SEQ ID NO:13 and a light chain variable region comprised in amino acid sequence of SEQ ID NO:14;
h) a heavy chain variable region comprised in amino acid sequence of SEQ ID NO:15 and a light chain variable region comprised in amino acid sequence of SEQ ID NO:16;
i) a heavy chain variable region comprised in amino acid sequence of SEQ ID NO:17 and a light chain variable region comprised in amino acid sequence of SEQ ID NO:18;
j) a heavy chain variable region comprised in amino acid sequence of SEQ ID NO:19 and a light chain variable region comprised in amino acid sequence of SEQ ID NO:20;
k) a heavy chain variable region comprised in amino acid sequence of SEQ ID NO:21 and a light chain variable region comprised in amino acid sequence of SEQ ID NO:22;
l) a heavy chain variable region comprised in amino acid sequence of SEQ ID NO:23 and a light chain variable region comprised in amino acid sequence of SEQ ID NO:24; or
m) a heavy chain variable region comprised in amino acid sequence of SEQ ID NO:25 and a light chain variable region comprised in amino acid sequence of SEQ ID NO:26.

3. The antibody according to claim 1, the antibody comprising:
a heavy chain variable region comprising a vhCDR1 comprising SEQ ID NO:51, a vhCDR2 comprising SEQ ID NO:52, a vhCDR3 comprising SEQ ID NO:53, and
a light chain variable region comprising a vlCDR1 comprising SEQ ID NO:54, a vlCDR2 comprising STS, and a vlCDR3 comprising SEQ ID NO:56.

4. The antibody according to claim 3, the antibody comprising:
a heavy chain variable region comprised in amino acid sequence of SEQ ID NO:9 and
a light chain variable region comprised in amino acid sequence of SEQ ID NO:10.

5. A composition comprising the antibody according to claim 1, and a pharmaceutical acceptable carrier or diluent.

6. The antibody according to claim 1, wherein the antibody comprises a constant region with an amino acid sequence at least 90% identical to a human IgG.

7. The antibody according to claim 6, wherein the human IgG is selected from a group consisting of IgG1, IgG2, IgG3 and IgG4.

8. The antibody according to claim 7, wherein the IgG is an IgG1.

9. The antibody according to claim 7, wherein the IgG is an IgG2.

10. A method of increasing levels of IL-6, IL-10, and TNF cytokines, decreasing levels of IL-2, IL-4, IL-5, IL-13, IL-17, and IFNγ, and inhibiting T cell proliferation in a subject, the method comprising administering to the subject an effective amount of the antibody according to claim 9 or a nucleic acid composition encoding said antibody,
wherein the antibody comprises a heavy chain variable region comprising a vhCDR1 of SEQ ID NO:51, a vhCDR2 of SEQ ID NO:52, and a vhCDR3 of SEQ ID NO:53, and
a light chain variable region comprising a vlCDR1 of SEQ ID NO:54, a vlCDR2 of STS, and a vlCDR3 of SEQ ID NO:56.

11. A method of treating an autoimmune disease in a subject comprising administering to the subject an effective amount of the antibody according to claim 9 or a nucleic acid composition encoding said antibody,
wherein the antibody comprises a heavy chain variable region comprising a vhCDR1 of SEQ ID NO:51, a vhCDR2 of SEQ ID NO:52, and a vhCDR3 of SEQ ID NO:53, and
a light chain variable region comprising a vlCDR1 of SEQ ID NO:54, a vlCDR2 of STS, and a vlCDR3 of SEQ ID NO:56.

12. A method according to claim 11, wherein the antibody is combined with one or more additional therapeutic agents to treat autoimmune disease.

13. A method of treating allergic inflammation in a subject comprising administering to the subject an effective amount of the antibody according to claim 9 or a nucleic acid composition encoding said antibody,
wherein the antibody comprises a heavy chain variable region comprising a vhCDR1 of SEQ ID NO:51, a vhCDR2 of SEQ ID NO:52, and a vhCDR3 of SEQ ID NO:53, and
a light chain variable region comprising a vlCDR1 of SEQ ID NO:54, a vlCDR2 of STS, and a vlCDR3 of SEQ ID NO:56.

14. A method according to claim 13, wherein the antibody is combined with one or more additional therapeutics to treat allergic inflammation.

15. A nucleic acid composition encoding the antibody according to claim 1, wherein a first nucleic acid encodes the heavy chain variable region, and wherein a second nucleic acid encodes the light chain variable region.

16. An expression vector composition comprising the nucleic acid composition according to claim 15, wherein the first nucleic acid is contained in a first expression vector and the second nucleic acid is contained in a second expression vector.

17. A host cell comprising the expression vector composition according to claim 16.

18. A method of making an antibody comprising culturing said host cell of claim 17 under conditions wherein the antibody is expressed, and recovering the antibody.

19. An expression vector composition comprising the nucleic acid composition according to claim 15, wherein the first nucleic acid and the second nucleic acid are contained in a single expression vector.

20. A host cell comprising the expression vector composition according to claim 19.

* * * * *

SEQUENCE LISTING

```
<160> NUMBER OF SEQ ID NOS: 104

<210> SEQ ID NO 1
<211> LENGTH: 288
<212> TYPE: PRT
<213> ORGANISM: Artificial Sequence
<220> FEATURE:
<223> OTHER INFORMATION: LILRB3 Heavy chain variable region (2E1)

<400> SEQUENCE: 1

Met Glu Trp Pro Cys Ile Phe Leu Phe Leu Leu Ser Val Thr Glu Gly
1               5                   10                  15

Val His Ser Gln Val Gln Leu Gln Gln Ser Gly Pro Glu Leu Val Lys
            20                  25                  30

Pro Gly Ala Ser Val Lys Ile Ser Cys Lys Ala Ser Asp Tyr Ala Phe
        35                  40                  45

Ser Ser Ser Trp Met Asn Trp Val Lys Gln Arg Pro Gly Lys Gly Leu
    50                  55                  60

Glu Trp Ile Gly Arg Ile Tyr Pro Gly Asp Gly Asp Thr Asn Tyr Asn
65                  70                  75                  80

Gly Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Glu Ile Tyr Tyr Asp Tyr Asp Gly Tyr Phe Asp
        115                 120                 125

Val Trp Gly Thr Gly Thr Thr Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Gln Thr Val Thr Cys Asn Val
```

```
                    210                 215                 220
Ala His Pro Ala Ser Ser Thr Lys Val Asp Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
                260                 265                 270

Thr Pro Lys Val Thr Cys Val Val Val Asp Ile Ser Lys Asp Asp Gln
                275                 280                 285

<210> SEQ ID NO 2
<211> LENGTH: 226
<212> TYPE: PRT
<213> ORGANISM: Artificial Sequence
<220> FEATURE:
<223> OTHER INFORMATION: LILRB3 Light chain variable region (2E1)

<400> SEQUENCE: 2

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
                20                  25                  30

Met Ser Ala Ser Pro Gly Glu Lys Val Thr Ile Thr Cys Ser Ala Ser
            35                  40                  45

Ser Ser Val Asn Tyr Met His Trp Phe Gln Gln Lys Ser Gly Thr Ser
        50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
                100                 105                 110

Ser Ser Tyr Pro Tyr Thr Phe Gly Gly Gly Thr Lys Leu Glu Ile Lys
            115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Arg Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
210                 215                 220

Pro Arg
225

<210> SEQ ID NO 3
<211> LENGTH: 286
<212> TYPE: PRT
<213> ORGANISM: Artificial Sequence
<220> FEATURE:
<223> OTHER INFORMATION: LILRB3 Heavy chain variable region (3A3)

<400> SEQUENCE: 3
```

```
Met Glu Trp Thr Trp Val Phe Leu Phe Leu Leu Ser Val Thr Ala Gly
1               5                   10                  15

Val His Ser Gln Val Gln Leu Gln Gln Ser Arg Thr Glu Leu Met Lys
            20                  25                  30

Pro Gly Ala Ser Val Lys Leu Ser Cys Lys Ala Thr Gly Tyr Thr Phe
            35                  40                  45

Thr Gly Tyr Trp Ile Glu Trp Val Lys Gln Arg Pro Gly His Gly Leu
        50                  55                  60

Glu Trp Ile Gly Glu Ile Leu Pro Gly Ser Thr Asn Ile Asn Tyr Asn
65                  70                  75                  80

Glu Arg Phe Lys Gly Lys Ala Thr Ile Thr Ala Asp Thr Ser Ser Asn
                85                  90                  95

Thr Ala Tyr Met Gln Leu Ser Ser Leu Thr Thr Glu Asp Ser Ala Ile
                100                 105                 110

Tyr Tyr Cys Ala Arg Trp Ala Ser Val Val Gly Asp Tyr Trp Gly
                115                 120                 125

Gln Gly Ala Thr Leu Thr Val Ser Ser Ala Lys Thr Thr Pro Pro Ser
        130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
                180                 185                 190

Val Leu Gln Ser Asp Leu Tyr Thr Leu Ser Ser Ser Val Thr Val Pro
                195                 200                 205

Ser Ser Thr Trp Pro Ser Gln Thr Val Thr Cys Asn Val Ala His Pro
        210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
                260                 265                 270

Val Thr Cys Val Val Val Asp Ile Ser Lys Asp Asp Gln Gly
        275                 280                 285

<210> SEQ ID NO 4
<211> LENGTH: 216
<212> TYPE: PRT
<213> ORGANISM: Artificial Sequence
<220> FEATURE:
<223> OTHER INFORMATION: LILRB3 Light chain variable region (3A3)

<400> SEQUENCE: 4

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
            35                  40                  45

Ser Ser Val Ser Ser Ser Tyr Leu His Trp Tyr Gln Gln Lys Pro Gly
        50                  55                  60

Ser Ser Pro Lys Leu Trp Ile Tyr Ser Thr Ser Asn Leu Ala Ser Gly
65                  70                  75                  80
```

```
Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Pro Thr Phe Gly Gly Gly Thr Lys Leu Glu
        115                 120                 125

Ile Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Arg Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr
210                 215

<210> SEQ ID NO 5
<211> LENGTH: 270
<212> TYPE: PRT
<213> ORGANISM: Artificial Sequence
<220> FEATURE:
<223> OTHER INFORMATION: LILRB3 Heavy chain variable region (3B1)

<400> SEQUENCE: 5

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Ser Ala Tyr Tyr Trp Asn Trp Ile Arg Gln Phe Pro Glu Asn Lys Leu
    50                  55                  60

Glu Trp Met Gly Tyr Ile Ser His Asp Gly Ser Asn Thr Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
            100                 105                 110

Tyr Cys Ala Thr Phe Asp Ser Asp Glu Val Tyr Trp Gly Gln Gly Thr
        115                 120                 125

Leu Val Thr Val Ser Ala Ala Lys Thr Thr Pro Pro Ser Val Tyr Pro
130                 135                 140

Leu Ala Pro Gly Cys Gly Asp Thr Thr Gly Ser Ser Val Thr Leu Gly
145                 150                 155                 160

Cys Leu Val Lys Gly Tyr Phe Pro Glu Ser Val Thr Val Thr Trp Asn
                165                 170                 175

Ser Gly Ser Leu Ser Ser Val His Thr Phe Pro Ala Leu Leu Gln
            180                 185                 190

Ser Gly Leu Tyr Thr Met Ser Ser Val Thr Val Pro Ser Ser Thr
        195                 200                 205

Trp Pro Ser Gln Thr Val Thr Cys Ser Val Ala His Pro Ala Ser Ser
210                 215                 220
```

-continued

```
Thr Thr Val Asp Lys Lys Leu Glu Pro Ser Gly Pro Ile Ser Thr Ile
225                 230                 235                 240

Asn Pro Cys Pro Pro Cys Lys Glu Cys His Lys Cys Pro Ala Pro Asn
                245                 250                 255

Leu Glu Gly Gly Pro Ser Val Phe Ile Phe Pro Pro Lys Gly
            260                 265                 270

<210> SEQ ID NO 6
<211> LENGTH: 212
<212> TYPE: PRT
<213> ORGANISM: Artificial Sequence
<220> FEATURE:
<223> OTHER INFORMATION: LILRB3 Light chain variable region (3B1)

<400> SEQUENCE: 6

Ser Val Leu Thr Gln Val Leu Ala Leu Leu Leu Trp Leu Thr Gly
1               5                   10                  15

Ala Arg Cys Asp Ile Gln Met Thr Gln Ser Pro Ala Ser Leu Ser Ala
                20                  25                  30

Ser Val Gly Glu Thr Val Thr Ile Thr Cys Arg Ala Ser Gly Asn Ile
            35                  40                  45

His Asn Phe Leu Ala Trp Tyr Gln Gln Lys Gly Arg Ser Pro Gln
 50                  55                  60

Leu Leu Val Tyr Asn Ala Lys Thr Leu Ala Asp Gly Val Pro Ser Arg
65                  70                  75                  80

Phe Ser Gly Ser Gly Ser Gly Ala Gln Tyr Ser Leu Lys Val Asn Ser
                85                  90                  95

Leu Gln Pro Glu Asp Phe Gly Asn Tyr Tyr Cys Gln His Phe Trp Ser
            100                 105                 110

Thr Pro Phe Thr Phe Gly Ser Gly Thr Lys Leu Glu Ala Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Arg Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr
    210

<210> SEQ ID NO 7
<211> LENGTH: 290
<212> TYPE: PRT
<213> ORGANISM: Artificial Sequence
<220> FEATURE:
<223> OTHER INFORMATION: LILRB3 Heavy chain variable region (6A10)

<400> SEQUENCE: 7

Met Gly Trp Ser Trp Ile Phe Leu Leu Phe Leu Ser Gly Thr Ala Gly
1               5                   10                  15

Val Leu Ser Glu Val Gln Leu Gln Gln Ser Gly Pro Glu Leu Val Lys
                20                  25                  30

Pro Gly Ala Ser Val Lys Ile Pro Cys Lys Ala Ser Gly Tyr Thr Phe
            35                  40                  45
```

-continued

```
Thr Asp Tyr Asn Met Asp Trp Val Lys Gln Ser His Gly Lys Ser Leu
    50                  55                  60

Glu Trp Ile Gly Asp Ile Asn Pro Asn Asn Gly Gly Thr Ile Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Arg Gly Ile Tyr Tyr Gly Ser Ser Tyr Ala Met
        115                 120                 125

Asp Tyr Trp Gly Gln Gly Thr Ser Val Thr Val Ser Ser Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Gln Thr Val Thr Cys Asn
    210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Val Asp Ile Ser Lys Asp Asp
        275                 280                 285

Gln Gly
    290

<210> SEQ ID NO 8
<211> LENGTH: 218
<212> TYPE: PRT
<213> ORGANISM: Artificial Sequence
<220> FEATURE:
<223> OTHER INFORMATION: LILRB3 Light chain variable region (6A10)

<400> SEQUENCE: 8

Met Glu Ser Gln Thr Gln Val Phe Leu Ser Leu Leu Leu Trp Val Ser
1               5                   10                  15

Gly Thr Cys Gly Asn Ile Met Met Thr Gln Ser Pro Ser Ser Leu Ala
                20                  25                  30

Val Ser Ala Gly Glu Lys Val Thr Met Ser Cys Lys Ser Ser Gln Ser
            35                  40                  45

Val Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Arg Val Gln Ala Glu Asp Leu Ala Val Tyr
            100                 105                 110
```

Tyr Cys His Gln Tyr Leu Ser Pro Tyr Thr Phe Gly Gly Gly Thr Lys
            115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Arg Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr
    210                 215

<210> SEQ ID NO 9
<211> LENGTH: 271
<212> TYPE: PRT
<213> ORGANISM: Artificial Sequence
<220> FEATURE:
<223> OTHER INFORMATION: LILRB3 Heavy chain variable region (7C5)

<400> SEQUENCE: 9

Met Glu Trp Glu Leu Ser Leu Ile Phe Ile Phe Ala Leu Leu Lys Asp
1               5                   10                  15

Val Gln Cys Asp Val Gln Leu Leu Glu Thr Gly Gly Gly Leu Val Gln
            20                  25                  30

Pro Gly Gly Ser Arg Gly Leu Ser Cys Glu Gly Ser Gly Phe Thr Phe
        35                  40                  45

Ser Gly Phe Trp Met Ser Trp Val Arg Gln Thr Pro Gly Lys Thr Leu
    50                  55                  60

Glu Trp Ile Gly Asp Ile Asn Ser Asp Gly Thr Ala Ile Asn Tyr Ala
65                  70                  75                  80

Pro Ser Ile Lys Asp Arg Phe Thr Ile Phe Arg Asp Asn Asp Lys Ser
                85                  90                  95

Thr Leu Tyr Leu Gln Met Ser Asn Val Arg Ser Glu Asp Thr Ala Thr
            100                 105                 110

Tyr Phe Cys Met Arg Ser Tyr Gly Ser Gly Pro Trp Cys Phe Asp Val
        115                 120                 125

Trp Gly Thr Gly Thr Thr Val Thr Val Ser Ser Ala Lys Thr Thr Ala
130                 135                 140

Pro Ser Val Tyr Pro Leu Ala Pro Val Cys Gly Gly Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Leu Leu Gln Ser Gly Leu Tyr Thr Leu Ser Ser Ser Val Thr
        195                 200                 205

Val Thr Ser Asn Thr Trp Pro Ser Gln Thr Ile Thr Cys Asn Val Ala
    210                 215                 220

His Pro Ala Ser Ser Thr Lys Val Asp Lys Lys Ile Glu Pro Arg Val
225                 230                 235                 240

Pro Ile Thr Gln Asn Pro Cys Pro Pro Leu Lys Glu Cys Pro Pro Cys
                245                 250                 255

-continued

```
Ala Ala Pro Asp Leu Leu Gly Gly Pro Ser Val Phe Ile Phe Pro
            260                 265                 270

<210> SEQ ID NO 10
<211> LENGTH: 170
<212> TYPE: PRT
<213> ORGANISM: Artificial Sequence
<220> FEATURE:
<223> OTHER INFORMATION: LILRB3 Light chain variable region (7C5)

<400> SEQUENCE: 10

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Ala Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Thr Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Phe Thr Phe Gly Ala Gly Thr Lys Leu Glu
        115                 120                 125

Leu Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Lys Gly Glu Phe
                165                 170

<210> SEQ ID NO 11
<211> LENGTH: 285
<212> TYPE: PRT
<213> ORGANISM: Artificial Sequence
<220> FEATURE:
<223> OTHER INFORMATION: LILRB3 Heavy chain variable region (1D5)

<400> SEQUENCE: 11

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Leu Ser Cys Lys Ser Thr Asp Tyr Thr Phe
        35                  40                  45

Thr Gly Tyr Trp Ile Glu Trp Val Lys Gln Arg Pro Gly His Gly Leu
    50                  55                  60

Glu Trp Ile Gly Glu Ile Leu Phe Gly Ser Thr Asn Asn Tyr Asn
65                  70                  75                  80

Glu Lys Phe Asn Gly Lys Ala Thr Phe Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Arg Arg Asn Asn Phe Tyr Phe Asp Tyr Trp Gly Gln
```

```
                115                 120                 125
Gly Thr Thr Leu Thr Val Ser Ser Ala Lys Thr Thr Pro Pro Ser Val
            130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Val Thr Val Pro Ser
            195                 200                 205

Ser Thr Trp Pro Ser Gln Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Gln Gly
                275                 280                 285

<210> SEQ ID NO 12
<211> LENGTH: 228
<212> TYPE: PRT
<213> ORGANISM: Artificial Sequence
<220> FEATURE:
<223> OTHER INFORMATION: LILRB3 Light chain variable region (1D5)

<400> SEQUENCE: 12

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Thr Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Thr Thr Met Glu Thr Glu Asp Ala Ala Thr Tyr Tyr Cys His
            100                 105                 110

Gln Tyr His Arg Ser Pro Phe Thr Phe Gly Ser Gly Thr Lys Leu Glu
        115                 120                 125

Ile Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Arg Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
```

```
                195                 200                 205
Tyr Glu Arg His Asn Ser Tyr Thr Cys Glu Ala Thr His Lys Thr Ser
    210                 215                 220

Thr Ser Pro Arg
225

<210> SEQ ID NO 13
<211> LENGTH: 285
<212> TYPE: PRT
<213> ORGANISM: Artificial Sequence
<220> FEATURE:
<223> OTHER INFORMATION: LILRB3 Heavy chain variable region (4C8)

<400> SEQUENCE: 13

Met Glu Trp Thr Trp Val Phe Leu Phe Leu Leu Ser Val Thr Ala Gly
1               5                   10                  15

Val His Ser Gln Val Gln Leu Gln Gln Ser Gly Gly Glu Leu Met Lys
                20                  25                  30

Pro Gly Ala Ser Val Lys Leu Ser Cys Lys Ala Thr Glu Tyr Thr Phe
            35                  40                  45

Thr Gly Tyr Trp Ile Glu Trp Ile Lys Gln Arg Pro Gly His Gly Leu
        50                  55                  60

Glu Trp Ile Gly Glu Ile Leu Phe Gly Asn Gly Val Thr Asn Tyr Asn
65                  70                  75                  80

Glu Asn Phe Lys Gly Lys Ala Thr Phe Thr Ala Asp Ala Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Arg Arg Thr Tyr Phe Tyr Phe Asp Tyr Trp Gly Gln
        115                 120                 125

Gly Thr Thr Leu Thr Val Ser Ser Ala Lys Thr Thr Pro Pro Ser Val
130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Gln Thr Val Thr Cys Asn Val Ala His Pro Ala
210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Gln Gly
        275                 280                 285

<210> SEQ ID NO 14
<211> LENGTH: 216
<212> TYPE: PRT
<213> ORGANISM: Artificial Sequence
<220> FEATURE:
<223> OTHER INFORMATION: LILRB3 Light chain variable region (4C8)
```

<400> SEQUENCE: 14

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Ser Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Phe Thr Phe Gly Ser Gly Thr Lys Leu Glu
        115                 120                 125

Ile Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Arg Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr
    210                 215

<210> SEQ ID NO 15
<211> LENGTH: 285
<212> TYPE: PRT
<213> ORGANISM: Artificial Sequence
<220> FEATURE:
<223> OTHER INFORMATION: LILRB3 Heavy chain variable region (7E10)

<400> SEQUENCE: 15

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Leu Ser Cys Lys Ala Ser Gly Tyr Thr Phe
        35                  40                  45

Thr Gly Tyr Trp Ile Glu Trp Val Lys Gln Arg Pro Gly His Gly Leu
    50                  55                  60

Glu Trp Ile Gly Glu Ile Leu Pro Gly Asn Gly Tyr Thr Asn Tyr Asn
65                  70                  75                  80

Glu Lys Phe Glu Gly Lys Ala Thr Phe Thr Ala Asp Thr Ser Ser Asn
                85                  90                  95

Thr Ala Tyr Ile Gln Leu Asn Ser Leu Thr Thr Glu Asp Ser Ala Ile
            100                 105                 110

Tyr Tyr Cys Ala Arg Arg Gly Ser Trp Thr Met Asp Phe Trp Gly Gln
        115                 120                 125

```
Gly Thr Ser Val Thr Val Ser Ser Ala Lys Thr Thr Pro Pro Ser Val
            130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
                180                 185                 190

Leu Gln Ser Asp Leu Tyr Thr Leu Ser Ser Ser Val Thr Val Pro Ser
            195                 200                 205

Ser Thr Trp Pro Ser Gln Thr Val Thr Cys Asn Val Ala His Pro Ala
210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
                260                 265                 270

Thr Cys Val Val Val Asp Ile Ser Lys Asp Asp Lys Gly
            275                 280                 285

<210> SEQ ID NO 16
<211> LENGTH: 216
<212> TYPE: PRT
<213> ORGANISM: Artificial Sequence
<220> FEATURE:
<223> OTHER INFORMATION: LILRB3 Light chain variable region (7E10)

<400> SEQUENCE: 16

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
                20                  25                  30

Met Ser Ala Ser Leu Glu Glu Arg Val Thr Met Thr Cys Thr Ala Ser
            35                  40                  45

Ser Ser Val Ser Ser Ser Tyr Leu His Trp Phe Gln Gln Lys Pro Gly
        50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro His Thr Phe Gly Gly Gly Thr Lys Leu Glu
        115                 120                 125

Ile Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Arg Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205
```

Tyr Glu Arg His Asn Ser Tyr Thr
    210                 215

<210> SEQ ID NO 17
<211> LENGTH: 286
<212> TYPE: PRT
<213> ORGANISM: Artificial Sequence
<220> FEATURE:
<223> OTHER INFORMATION: LILRB3 Heavy chain variable region (9E8)

<400> SEQUENCE: 17

Met Glu Trp Ile Trp Ile Leu Leu Phe Ile Leu Ser Gly Thr Ala Gly
1               5                   10                  15

Val Gln Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Ser Asn Gly Ile Ser Trp Val Lys Gln Thr Thr Gly Gln Gly Leu
    50                  55                  60

Glu Trp Ile Gly Leu Ile Tyr Pro Arg Ser Gly Asn Thr Tyr Tyr Asn
65                  70                  75                  80

Glu Arg Phe Lys Gly Lys Ala Thr Leu Thr Ala Asp Lys Ser Ser Ser
                85                  90                  95

Thr Ala Tyr Met Glu Leu Arg Arg Leu Thr Ser Glu Asp Ser Ala Val
            100                 105                 110

Tyr Phe Cys Leu Arg Glu Arg Glu Thr Gly Leu Phe Asp Phe Trp Gly
        115                 120                 125

Gln Gly Thr Thr Leu Thr Val Ser Ser Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Gln Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Gln Gly
        275                 280                 285

<210> SEQ ID NO 18
<211> LENGTH: 214
<212> TYPE: PRT
<213> ORGANISM: Artificial Sequence
<220> FEATURE:
<223> OTHER INFORMATION: LILRB3 Light chain variable region (9E8)

<400> SEQUENCE: 18

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
            35                  40                  45

Ser Ser Val Ser Tyr Met His Trp Phe Gln Gln Lys Pro Gly Thr Ser
50                  55                  60

Pro Lys Leu Trp Ile Tyr Thr Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Pro Thr Phe Gly Gly Gly Thr Lys Leu Glu Val Lys
            115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Arg Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Lys Asp Glu Tyr Glu
            195                 200                 205

Arg His Asn Ser Tyr Thr
            210

<210> SEQ ID NO 19
<211> LENGTH: 284
<212> TYPE: PRT
<213> ORGANISM: Artificial Sequence
<220> FEATURE:
<223> OTHER INFORMATION: LILRB3 Heavy chain variable region (3E8)

<400> SEQUENCE: 19

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Arg Leu Ser Cys Lys Ala Thr Gly Tyr Thr Phe
            35                  40                  45

Thr Gly Tyr Trp Ile Glu Trp Val Lys Gln Arg Pro Gly His Gly Leu
50                  55                  60

Glu Trp Ile Gly Glu Ile Leu Pro Gly Ser Gly Ser Asn Tyr Asn
65                  70                  75                  80

Glu Lys Phe Lys Gly Lys Ala Thr Ile Thr Ala Asp Thr Ser Ser Asn
                85                  90                  95

Thr Ser Asp Met Gln Leu Asn Ser Leu Thr Thr Glu Asp Ser Ala Ile
            100                 105                 110

Tyr Tyr Cys Ala Arg Trp Gly His Pro Phe Asp Tyr Trp Gly Leu Gly
            115                 120                 125

Thr Thr Leu Thr Val Ser Ser Ala Lys Thr Thr Pro Pro Ser Val Tyr
130                 135                 140

Pro Leu Ala Pro Gly Ser Ala Ala Gln Thr Asn Ser Met Val Thr Leu
145                 150                 155                 160

```
Gly Cys Leu Val Lys Gly Tyr Phe Pro Glu Pro Val Thr Val Thr Trp
            165                 170                 175

Asn Ser Gly Ser Leu Ser Ser Gly Val His Thr Phe Pro Ala Val Leu
        180                 185                 190

Gln Ser Asp Leu Tyr Thr Leu Ser Ser Val Thr Val Pro Ser Ser
        195                 200                 205

Thr Trp Pro Ser Gln Thr Val Thr Cys Asn Val Ala His Pro Ala Ser
    210                 215                 220

Ser Thr Lys Val Asp Lys Lys Ile Val Pro Arg Asp Cys Gly Cys Lys
225                 230                 235                 240

Pro Cys Ile Cys Thr Val Pro Glu Val Ser Ser Val Phe Ile Phe Pro
            245                 250                 255

Pro Lys Pro Lys Asp Val Leu Thr Ile Thr Leu Thr Pro Lys Val Thr
            260                 265                 270

Cys Val Val Val Asp Ile Ser Lys Asp Asp Gln Gly
            275                 280

<210> SEQ ID NO 20
<211> LENGTH: 216
<212> TYPE: PRT
<213> ORGANISM: Artificial Sequence
<220> FEATURE:
<223> OTHER INFORMATION: LILRB3 Light chain variable region (3E8)

<400> SEQUENCE: 20

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Ser Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Arg Thr Phe Gly Gly Gly Thr Lys Leu Glu
        115                 120                 125

Ile Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Arg Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr
    210                 215

<210> SEQ ID NO 21
```

<211> LENGTH: 296
<212> TYPE: PRT
<213> ORGANISM: Artificial Sequence
<220> FEATURE:
<223> OTHER INFORMATION: LILRB3 Heavy chain variable region (5C1)

<400> SEQUENCE: 21

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Leu Ser Cys Lys Ala Thr Asp Tyr Thr Phe
        35                  40                  45

Thr Gly Tyr Trp Ile Glu Trp Val Lys Gln Arg Pro Gly His Gly Leu
    50                  55                  60

Glu Trp Ile Gly Gln Ile Leu Pro Gly Ser Ala Tyr Ser Asn Tyr Asn
65                  70                  75                  80

Glu Lys Phe Gln Gly Lys Ala Thr Phe Thr Ala Asp Thr Ser Ser Asp
                85                  90                  95

Thr Ala Phe Met Gln Leu Ser Ser Leu Thr Ala Glu Asp Ser Ala Ile
            100                 105                 110

Tyr Tyr Cys Ala Arg Arg Asp Tyr Tyr Thr Met Asp Tyr Trp Gly Gln
        115                 120                 125

Gly Thr Ser Val Thr Val Ser Ser Ala Lys Thr Thr Ala Pro Ser Val
    130                 135                 140

Tyr Pro Leu Ala Pro Val Cys Gly Gly Thr Thr Gly Ser Ser Val Thr
145                 150                 155                 160

Leu Gly Cys Leu Val Lys Gly Tyr Phe Pro Glu Pro Val Thr Leu Thr
                165                 170                 175

Trp Asn Ser Gly Ser Leu Ser Ser Gly Val His Thr Phe Pro Ala Leu
            180                 185                 190

Leu Gln Ser Gly Leu Tyr Thr Leu Ser Ser Ser Val Thr Val Thr Ser
        195                 200                 205

Asn Thr Trp Pro Ser Gln Thr Ile Thr Cys Asn Val Ala His Pro Ala
    210                 215                 220

Ser Ser Thr Lys Val Asp Lys Lys Ile Glu Pro Arg Val Pro Ile Thr
225                 230                 235                 240

Gln Asn Pro Cys Pro Pro Leu Lys Glu Cys Pro Pro Cys Ala Ala Pro
                245                 250                 255

Asp Leu Leu Gly Gly Pro Ser Val Phe Ile Phe Pro Pro Lys Ile Lys
            260                 265                 270

Asp Val Leu Met Ile Ser Leu Ser Pro Met Val Thr Cys Val Val Val
        275                 280                 285

Asp Val Ser Glu Asp Asp Gln Gly
    290                 295

<210> SEQ ID NO 22
<211> LENGTH: 216
<212> TYPE: PRT
<213> ORGANISM: Artificial Sequence
<220> FEATURE:
<223> OTHER INFORMATION: LILRB3 Light chain variable region (5C1)

<400> SEQUENCE: 22

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile

-continued

```
                       20                  25                  30

Met Ser Ala Ser Leu Gly Glu Arg Val Thr Met Thr Cys Thr Ala Ser
                35                  40                  45

Ser Ser Val Ser Ser Thr Tyr Leu His Trp Tyr Gln Gln Lys Pro Gly
        50                  55                  60

Ser Ser Pro Lys Leu Trp Ile Tyr Ser Thr Ser Asn Leu Ala Ser Gly
65                  70                  75                  80

Val Pro Pro Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Phe Thr Phe Gly Ser Gly Thr Lys Leu Glu
        115                 120                 125

Ile Glu Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Arg Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr
    210                 215

<210> SEQ ID NO 23
<211> LENGTH: 285
<212> TYPE: PRT
<213> ORGANISM: Artificial Sequence
<220> FEATURE:
<223> OTHER INFORMATION: LILRB3 Heavy chain variable region (9A1)

<400> SEQUENCE: 23

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
                20                  25                  30

Pro Gly Ala Ser Val Lys Leu Ser Cys Lys Ala Thr Gly Ser Thr Phe
            35                  40                  45

Thr Gly Tyr Trp Ile Glu Trp Val Lys Gln Arg Pro Gly His Gly Leu
        50                  55                  60

Glu Trp Ile Gly Glu Ile Leu Pro Gly Ser Gly Tyr Thr Asn Tyr Asn
65                  70                  75                  80

Glu Asn Phe Lys Gly Lys Ala Thr Ile Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Arg Arg Glu Trp Tyr Tyr Phe Asp Tyr Trp Gly Gln
        115                 120                 125

Gly Thr Thr Leu Ile Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
```

```
                    165                 170                 175
Trp Asn Ser Gly Ser Leu Ser Ser Gly Val His Thr Phe Pro Ala Val
                180                 185                 190

Leu Gln Ser Asp Leu Tyr Thr Leu Ser Ser Val Thr Val Pro Ser
            195                 200                 205

Ser Thr Trp Pro Ser Gln Thr Val Thr Cys Asn Val Ala His Pro Ala
        210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
                260                 265                 270

Thr Cys Val Val Val Asp Ile Ser Lys Asp Asp Gln Gly
                275                 280                 285

<210> SEQ ID NO 24
<211> LENGTH: 216
<212> TYPE: PRT
<213> ORGANISM: Artificial Sequence
<220> FEATURE:
<223> OTHER INFORMATION: LILRB3 Light chain variable region (9A1)

<400> SEQUENCE: 24

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Ser Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ile Met Glu Ala Glu Asp Ala Ala Thr Tyr Tyr Cys His
            100                 105                 110

Gln Tyr His Arg Ser Pro Phe Thr Phe Gly Ser Gly Thr Lys Leu Asp
        115                 120                 125

Ile Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Arg Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr
    210                 215

<210> SEQ ID NO 25
<211> LENGTH: 285
<212> TYPE: PRT
```

<213> ORGANISM: Artificial Sequence
<220> FEATURE:
<223> OTHER INFORMATION: LILRB3 Heavy chain variable region (1B2)

<400> SEQUENCE: 25

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Leu Ser Cys Lys Ala Thr Gly Tyr Thr Phe
        35                  40                  45

Thr Val Tyr Trp Ile Glu Trp Val Lys Gln Arg Pro Gly His Gly Leu
    50                  55                  60

Glu Trp Ile Gly Glu Ile Leu Pro Gly Ser Gly Ser Ile Asn Tyr Ile
65                  70                  75                  80

Glu Lys Phe Lys Gly Lys Ala Thr Ile Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Arg Arg Thr Trp Tyr Tyr Phe Asp Tyr Trp Gly Gln
        115                 120                 125

Gly Thr Thr Leu Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Gln Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Gln Gly
        275                 280                 285

<210> SEQ ID NO 26
<211> LENGTH: 216
<212> TYPE: PRT
<213> ORGANISM: Artificial Sequence
<220> FEATURE:
<223> OTHER INFORMATION: LILRB3 Light chain variable region (1B2)

<400> SEQUENCE: 26

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

```
Ser Ser Val Ser Ser Ser Tyr Leu His Trp Tyr Gln Gln Lys Pro Gly
 50                  55                  60

Ser Ser Pro Gln Leu Trp Ile Tyr Ser Thr Ser Asn Leu Ala Ser Gly
 65                  70                  75                  80

Val Pro Thr Arg Phe Ser Gly Ser Gly Thr Ser Tyr Ser Leu
                 85                  90                  95

Thr Ile Ser Ser Met Glu Ala Glu Asp Ala Ala Thr Tyr Tyr Cys His
                100                 105                 110

Gln Tyr His Arg Ser Pro Phe Thr Phe Gly Ser Gly Thr Lys Leu Glu
             115                 120                 125

Ile Lys Arg Ala Asp Ala Ala Pro Thr Val Ser Ile Phe Pro Pro Ser
 130                 135                 140

Ser Glu Gln Leu Thr Ser Gly Gly Ala Ser Val Val Cys Phe Leu Asn
 145                 150                 155                 160

Asn Phe Tyr Pro Arg Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
             180                 185                 190

Asp Ser Thr Tyr Ser Met Ser Ser Thr Leu Thr Leu Thr Lys Asp Glu
         195                 200                 205

Tyr Glu Arg His Asn Ser Tyr Thr
 210                 215

<210> SEQ ID NO 27
<211> LENGTH: 8
<212> TYPE: PRT
<213> ORGANISM: Artificial Sequence
<220> FEATURE:
<223> OTHER INFORMATION: LILRB3 Heavy chain variable region CDR1 (2E1)

<400> SEQUENCE: 27

Asp Tyr Ala Phe Ser Ser Ser Trp
1               5

<210> SEQ ID NO 28
<211> LENGTH: 8
<212> TYPE: PRT
<213> ORGANISM: Artificial Sequence
<220> FEATURE:
<223> OTHER INFORMATION: LILRB3 Heavy chain variable region CDR2 (2E1)

<400> SEQUENCE: 28

Ile Tyr Pro Gly Asp Gly Asp Thr
1               5

<210> SEQ ID NO 29
<211> LENGTH: 14
<212> TYPE: PRT
<213> ORGANISM: Artificial Sequence
<220> FEATURE:
<223> OTHER INFORMATION: LILRB3 Heavy chain variable region CDR3 (2E1)

<400> SEQUENCE: 29

Ala Arg Glu Ile Tyr Tyr Asp Tyr Asp Gly Tyr Phe Asp Val
1               5                   10

<210> SEQ ID NO 30
<211> LENGTH: 5
<212> TYPE: PRT
<213> ORGANISM: Artificial Sequence
<220> FEATURE:
<223> OTHER INFORMATION: LILRB3 Light chain variable region CDR1 (2E1)
```

```
<400> SEQUENCE: 30

Ser Ser Val Asn Tyr
1               5

<210> SEQ ID NO 31

<400> SEQUENCE: 31

000

<210> SEQ ID NO 32
<211> LENGTH: 9
<212> TYPE: PRT
<213> ORGANISM: Artificial Sequence
<220> FEATURE:
<223> OTHER INFORMATION: LILRB3 Light chain variable region CDR3 (2E1)

<400> SEQUENCE: 32

Cys Gln Gln Arg Ser Ser Tyr Pro Tyr
1               5

<210> SEQ ID NO 33
<211> LENGTH: 8
<212> TYPE: PRT
<213> ORGANISM: Artificial Sequence
<220> FEATURE:
<223> OTHER INFORMATION: LILRB3 Heavy chain variable region CDR1 (3A3)

<400> SEQUENCE: 33

Gly Tyr Thr Phe Thr Gly Tyr Trp
1               5

<210> SEQ ID NO 34
<211> LENGTH: 8
<212> TYPE: PRT
<213> ORGANISM: Artificial Sequence
<220> FEATURE:
<223> OTHER INFORMATION: LILRB3 Heavy chain variable region CDR2 (3A3)

<400> SEQUENCE: 34

Ile Leu Pro Gly Ser Thr Asn Ile
1               5

<210> SEQ ID NO 35
<211> LENGTH: 11
<212> TYPE: PRT
<213> ORGANISM: Artificial Sequence
<220> FEATURE:
<223> OTHER INFORMATION: LILRB3 Heavy chain variable region CDR3 (3A3)

<400> SEQUENCE: 35

Ala Arg Trp Ala Ser Val Val Val Gly Asp Tyr
1               5                   10

<210> SEQ ID NO 36
<211> LENGTH: 7
<212> TYPE: PRT
<213> ORGANISM: Artificial Sequence
<220> FEATURE:
<223> OTHER INFORMATION: LILRB3 Light chain variable region CDR1 (3A3)

<400> SEQUENCE: 36

Ser Ser Val Ser Ser Ser Tyr
1               5
```

```
<210> SEQ ID NO 37

<400> SEQUENCE: 37

000

<210> SEQ ID NO 38
<211> LENGTH: 9
<212> TYPE: PRT
<213> ORGANISM: Artificial Sequence
<220> FEATURE:
<223> OTHER INFORMATION: LILRB3 Light chain variable region CDR3 (3A3)

<400> SEQUENCE: 38

His Gln Tyr His Arg Ser Pro Pro Thr
1               5

<210> SEQ ID NO 39
<211> LENGTH: 8
<212> TYPE: PRT
<213> ORGANISM: Artificial Sequence
<220> FEATURE:
<223> OTHER INFORMATION: LILRB3 Heavy chain variable region CDR1 (3B1)

<400> SEQUENCE: 39

Tyr Ser Ile Thr Ser Ala Tyr Tyr
1               5

<210> SEQ ID NO 40
<211> LENGTH: 7
<212> TYPE: PRT
<213> ORGANISM: Artificial Sequence
<220> FEATURE:
<223> OTHER INFORMATION: LILRB3 Heavy chain variable region CDR2 (3B1)

<400> SEQUENCE: 40

Ile Ser His Asp Gly Ser Asn
1               5

<210> SEQ ID NO 41
<211> LENGTH: 9
<212> TYPE: PRT
<213> ORGANISM: Artificial Sequence
<220> FEATURE:
<223> OTHER INFORMATION: LILRB3 Heavy chain variable region CDR3 (3B1)

<400> SEQUENCE: 41

Ala Thr Phe Asp Ser Asp Glu Val Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: LILRB3 Light chain variable region CDR1 (3B1)

<400> SEQUENCE: 42

Gly Asn Ile His Asn Phe
1               5

<210> SEQ ID NO 43

<400> SEQUENCE: 43

000
```

```
<210> SEQ ID NO 44
<211> LENGTH: 9
<212> TYPE: PRT
<213> ORGANISM: Artificial Sequence
<220> FEATURE:
<223> OTHER INFORMATION: LILRB3 Light chain variable region CDR3 (3B1)

<400> SEQUENCE: 44

Gln His Phe Trp Ser Thr Pro Phe Thr
1               5

<210> SEQ ID NO 45
<211> LENGTH: 8
<212> TYPE: PRT
<213> ORGANISM: Artificial Sequence
<220> FEATURE:
<223> OTHER INFORMATION: LILRB3 Heavy chain variable region CDR1 (6A10)

<400> SEQUENCE: 45

Gly Tyr Thr Phe Thr Asp Tyr Asn
1               5

<210> SEQ ID NO 46
<211> LENGTH: 8
<212> TYPE: PRT
<213> ORGANISM: Artificial Sequence
<220> FEATURE:
<223> OTHER INFORMATION: LILRB3 Heavy chain variable region CDR2 (6A10)

<400> SEQUENCE: 46

Ile Asn Pro Asn Asn Gly Gly Thr
1               5

<210> SEQ ID NO 47
<211> LENGTH: 15
<212> TYPE: PRT
<213> ORGANISM: Artificial Sequence
<220> FEATURE:
<223> OTHER INFORMATION: LILRB3 Heavy chain variable region CDR3 (6A10)

<400> SEQUENCE: 47

Ala Arg Arg Gly Ile Tyr Tyr Gly Ser Ser Tyr Ala Met Asp Tyr
1               5                   10                  15

<210> SEQ ID NO 48
<211> LENGTH: 12
<212> TYPE: PRT
<213> ORGANISM: Artificial Sequence
<220> FEATURE:
<223> OTHER INFORMATION: LILRB3 Light chain variable region CDR1 (6A10)

<400> SEQUENCE: 48

Gln Ser Val Leu Tyr Ser Ser Asn Gln Lys Asn Tyr
1               5                   10

<210> SEQ ID NO 49

<400> SEQUENCE: 49

000

<210> SEQ ID NO 50
<211> LENGTH: 8
<212> TYPE: PRT
<213> ORGANISM: Artificial Sequence
<220> FEATURE:
<223> OTHER INFORMATION: LILRB3 Light chain variable region CDR3 ((6A10)
```

```
<400> SEQUENCE: 50

His Gln Tyr Leu Ser Pro Tyr Thr
1               5

<210> SEQ ID NO 51
<211> LENGTH: 7
<212> TYPE: PRT
<213> ORGANISM: Artificial Sequence
<220> FEATURE:
<223> OTHER INFORMATION: LILRB3 Heavy chain variable region CDR1 (7C5)

<400> SEQUENCE: 51

Gly Phe Thr Phe Ser Gly Phe
1               5

<210> SEQ ID NO 52
<211> LENGTH: 8
<212> TYPE: PRT
<213> ORGANISM: Artificial Sequence
<220> FEATURE:
<223> OTHER INFORMATION: LILRB3 Heavy chain variable region CDR2 (7C5)

<400> SEQUENCE: 52

Ile Asn Ser Asp Gly Thr Ala Ile
1               5

<210> SEQ ID NO 53
<211> LENGTH: 13
<212> TYPE: PRT
<213> ORGANISM: Artificial Sequence
<220> FEATURE:
<223> OTHER INFORMATION: LILRB3 Heavy chain variable region CDR3 (7C5)

<400> SEQUENCE: 53

Met Arg Ser Tyr Gly Ser Gly Pro Trp Cys Phe Asp Val
1               5                   10

<210> SEQ ID NO 54
<211> LENGTH: 7
<212> TYPE: PRT
<213> ORGANISM: Artificial Sequence
<220> FEATURE:
<223> OTHER INFORMATION: LILRB3 Light chain variable region CDR1 (7C5)

<400> SEQUENCE: 54

Ser Ser Val Ser Ser Ala Tyr
1               5

<210> SEQ ID NO 55

<400> SEQUENCE: 55

000

<210> SEQ ID NO 56
<211> LENGTH: 8
<212> TYPE: PRT
<213> ORGANISM: Artificial Sequence
<220> FEATURE:
<223> OTHER INFORMATION: LILRB3 Light chain variable region CDR3 (7C5)

<400> SEQUENCE: 56

Gln Tyr His Arg Ser Pro Phe Thr
1               5

<210> SEQ ID NO 57
```

```
<211> LENGTH: 8
<212> TYPE: PRT
<213> ORGANISM: Artificial Sequence
<220> FEATURE:
<223> OTHER INFORMATION: LILRB3 Heavy chain variable region CDR1 (1D5)

<400> SEQUENCE: 57

Asp Tyr Thr Phe Thr Gly Tyr Trp
1               5

<210> SEQ ID NO 58
<211> LENGTH: 8
<212> TYPE: PRT
<213> ORGANISM: Artificial Sequence
<220> FEATURE:
<223> OTHER INFORMATION: LILRB3 Heavy chain variable region CDR2 (1D5)

<400> SEQUENCE: 58

Ile Leu Phe Gly Ser Gly Thr Asn
1               5

<210> SEQ ID NO 59
<211> LENGTH: 11
<212> TYPE: PRT
<213> ORGANISM: Artificial Sequence
<220> FEATURE:
<223> OTHER INFORMATION: LILRB3 Heavy chain variable region CDR3 (1D5)

<400> SEQUENCE: 59

Cys Ala Arg Arg Asn Asn Phe Tyr Phe Asp Tyr
1               5                   10

<210> SEQ ID NO 60
<211> LENGTH: 6
<212> TYPE: PRT
<213> ORGANISM: Artificial Sequence
<220> FEATURE:
<223> OTHER INFORMATION: LILRB3 Light chain variable region CDR1 (1D5)

<400> SEQUENCE: 60

Ser Ser Val Ser Ser Thr
1               5

<210> SEQ ID NO 61

<400> SEQUENCE: 61

000

<210> SEQ ID NO 62
<211> LENGTH: 9
<212> TYPE: PRT
<213> ORGANISM: Artificial Sequence
<220> FEATURE:
<223> OTHER INFORMATION: LILRB3 Light chain variable region CDR3 (1D5)

<400> SEQUENCE: 62

His Gln Tyr His Arg Ser Pro Phe Thr
1               5

<210> SEQ ID NO 63
<211> LENGTH: 8
<212> TYPE: PRT
<213> ORGANISM: Artificial Sequence
<220> FEATURE:
<223> OTHER INFORMATION: LILRB3 Heavy chain variable region CDR1 (4C8)

<400> SEQUENCE: 63
```

Glu Tyr Thr Phe Thr Gly Tyr Trp
1               5

<210> SEQ ID NO 64
<211> LENGTH: 8
<212> TYPE: PRT
<213> ORGANISM: Artificial Sequence
<220> FEATURE:
<223> OTHER INFORMATION: LILRB3 Heavy chain variable region CDR2 (4C8)

<400> SEQUENCE: 64

Ile Leu Phe Gly Asn Gly Val Thr
1               5

<210> SEQ ID NO 65
<211> LENGTH: 10
<212> TYPE: PRT
<213> ORGANISM: Artificial Sequence
<220> FEATURE:
<223> OTHER INFORMATION: LILRB3 Heavy chain variable region CDR3 (4C8)

<400> SEQUENCE: 65

Ala Arg Arg Thr Tyr Phe Tyr Phe Asp Tyr
1               5                   10

<210> SEQ ID NO 66
<211> LENGTH: 7
<212> TYPE: PRT
<213> ORGANISM: Artificial Sequence
<220> FEATURE:
<223> OTHER INFORMATION: LILRB3 Light chain variable region CDR1 (4C8)

<400> SEQUENCE: 66

Ser Ser Val Ser Ser Ser Tyr
1               5

<210> SEQ ID NO 67

<400> SEQUENCE: 67

000

<210> SEQ ID NO 68
<211> LENGTH: 9
<212> TYPE: PRT
<213> ORGANISM: Artificial Sequence
<220> FEATURE:
<223> OTHER INFORMATION: LILRB3 Light chain variable region CDR3 (4C8)

<400> SEQUENCE: 68

His Gln Tyr His Arg Ser Pro Phe Thr
1               5

<210> SEQ ID NO 69
<211> LENGTH: 8
<212> TYPE: PRT
<213> ORGANISM: Artificial Sequence
<220> FEATURE:
<223> OTHER INFORMATION: LILRB3 Heavy chain variable region CDR1 (7E10)

<400> SEQUENCE: 69

Gly Tyr Thr Phe Thr Gly Tyr Trp
1               5

<210> SEQ ID NO 70
<211> LENGTH: 8

```
<212> TYPE: PRT
<213> ORGANISM: Artificial Sequence
<220> FEATURE:
<223> OTHER INFORMATION: LILRB3 Heavy chain variable region CDR2 (7E10)

<400> SEQUENCE: 70

Ile Leu Pro Gly Asn Gly Tyr Thr
1               5

<210> SEQ ID NO 71
<211> LENGTH: 10
<212> TYPE: PRT
<213> ORGANISM: Artificial Sequence
<220> FEATURE:
<223> OTHER INFORMATION: LILRB3 Heavy chain variable region CDR3 (7E10)

<400> SEQUENCE: 71

Ala Arg Arg Gly Ser Trp Thr Met Asp Phe
1               5                   10

<210> SEQ ID NO 72
<211> LENGTH: 7
<212> TYPE: PRT
<213> ORGANISM: Artificial Sequence
<220> FEATURE:
<223> OTHER INFORMATION: LILRB3 Light chain variable region CDR1 (7E10)

<400> SEQUENCE: 72

Ser Ser Val Ser Ser Ser Tyr
1               5

<210> SEQ ID NO 73

<400> SEQUENCE: 73

000

<210> SEQ ID NO 74
<211> LENGTH: 9
<212> TYPE: PRT
<213> ORGANISM: Artificial Sequence
<220> FEATURE:
<223> OTHER INFORMATION: LILRB3 Light chain variable region CDR3 (7E10)

<400> SEQUENCE: 74

His Gln Tyr His Arg Ser Pro His Thr
1               5

<210> SEQ ID NO 75
<211> LENGTH: 8
<212> TYPE: PRT
<213> ORGANISM: Artificial Sequence
<220> FEATURE:
<223> OTHER INFORMATION: LILRB3 Heavy chain variable region CDR1 (9E8)

<400> SEQUENCE: 75

Gly Tyr Thr Phe Thr Ser Asn Gly
1               5

<210> SEQ ID NO 76
<211> LENGTH: 8
<212> TYPE: PRT
<213> ORGANISM: Artificial Sequence
<220> FEATURE:
<223> OTHER INFORMATION: LILRB3 Heavy chain variable region CDR2 (9E8)

<400> SEQUENCE: 76
```

Ile Tyr Pro Arg Ser Gly Asn Thr
1               5

<210> SEQ ID NO 77
<211> LENGTH: 11
<212> TYPE: PRT
<213> ORGANISM: Artificial Sequence
<220> FEATURE:
<223> OTHER INFORMATION: LILRB3 Heavy chain variable region CDR3 (9E8)

<400> SEQUENCE: 77

Leu Arg Glu Arg Glu Thr Gly Leu Phe Asp Phe
1               5                   10

<210> SEQ ID NO 78
<211> LENGTH: 5
<212> TYPE: PRT
<213> ORGANISM: Artificial Sequence
<220> FEATURE:
<223> OTHER INFORMATION: LILRB3 Light chain variable region CDR1 (9E8)

<400> SEQUENCE: 78

Ser Ser Val Ser Tyr
1               5

<210> SEQ ID NO 79

<400> SEQUENCE: 79

000

<210> SEQ ID NO 80
<211> LENGTH: 9
<212> TYPE: PRT
<213> ORGANISM: Artificial Sequence
<220> FEATURE:
<223> OTHER INFORMATION: LILRB3 Light chain variable region CDR3 (9E8)

<400> SEQUENCE: 80

Gln Gln Arg Ser Ser Tyr Pro Pro Thr
1               5

<210> SEQ ID NO 81
<211> LENGTH: 8
<212> TYPE: PRT
<213> ORGANISM: Artificial Sequence
<220> FEATURE:
<223> OTHER INFORMATION: LILRB3 Heavy chain variable region CDR1 (3E8)

<400> SEQUENCE: 81

Gly Tyr Thr Phe Thr Gly Tyr Trp
1               5

<210> SEQ ID NO 82
<211> LENGTH: 8
<212> TYPE: PRT
<213> ORGANISM: Artificial Sequence
<220> FEATURE:
<223> OTHER INFORMATION: LILRB3 Heavy chain variable region CDR2 (3E8)

<400> SEQUENCE: 82

Ile Leu Pro Gly Ser Gly Ser Ser
1               5

<210> SEQ ID NO 83
<211> LENGTH: 8
<212> TYPE: PRT

<213> ORGANISM: Artificial Sequence
<220> FEATURE:
<223> OTHER INFORMATION: LILRB3 Heavy chain variable region CDR3 (3E8)

<400> SEQUENCE: 83

Arg Trp Gly His Pro Phe Asp Tyr
1               5

<210> SEQ ID NO 84
<211> LENGTH: 7
<212> TYPE: PRT
<213> ORGANISM: Artificial Sequence
<220> FEATURE:
<223> OTHER INFORMATION: LILRB3 Light chain variable region CDR1 (3E8)

<400> SEQUENCE: 84

Ser Ser Val Ser Ser Ser Tyr
1               5

<210> SEQ ID NO 85

<400> SEQUENCE: 85

000

<210> SEQ ID NO 86
<211> LENGTH: 9
<212> TYPE: PRT
<213> ORGANISM: Artificial Sequence
<220> FEATURE:
<223> OTHER INFORMATION: LILRB3 Light chain variable region CDR3 (3E8)

<400> SEQUENCE: 86

His Gln Tyr His Arg Ser Pro Arg Thr
1               5

<210> SEQ ID NO 87
<211> LENGTH: 8
<212> TYPE: PRT
<213> ORGANISM: Artificial Sequence
<220> FEATURE:
<223> OTHER INFORMATION: LILRB3 Heavy chain variable region CDR1 (5C1)

<400> SEQUENCE: 87

Asp Tyr Thr Phe Thr Gly Tyr Trp
1               5

<210> SEQ ID NO 88
<211> LENGTH: 8
<212> TYPE: PRT
<213> ORGANISM: Artificial Sequence
<220> FEATURE:
<223> OTHER INFORMATION: LILRB3 Heavy chain variable region CDR2 (5C1)

<400> SEQUENCE: 88

Ile Leu Pro Gly Ser Ala Tyr Ser
1               5

<210> SEQ ID NO 89
<211> LENGTH: 10
<212> TYPE: PRT
<213> ORGANISM: Artificial Sequence
<220> FEATURE:
<223> OTHER INFORMATION: LILRB3 Heavy chain variable region CDR3 (5C1)

<400> SEQUENCE: 89

Ala Arg Arg Asp Tyr Tyr Thr Met Asp Tyr

```
<210> SEQ ID NO 90
<211> LENGTH: 7
<212> TYPE: PRT
<213> ORGANISM: Artificial Sequence
<220> FEATURE:
<223> OTHER INFORMATION: LILRB3 Light chain variable region CDR1 (5C1)

<400> SEQUENCE: 90

Ser Ser Val Ser Ser Thr Tyr
1               5

<210> SEQ ID NO 91

<400> SEQUENCE: 91

000

<210> SEQ ID NO 92
<211> LENGTH: 9
<212> TYPE: PRT
<213> ORGANISM: Artificial Sequence
<220> FEATURE:
<223> OTHER INFORMATION: LILRB3 Light chain variable region CDR3 (5C1)

<400> SEQUENCE: 92

His Gln Tyr His Arg Ser Pro Phe Thr
1               5

<210> SEQ ID NO 93
<211> LENGTH: 7
<212> TYPE: PRT
<213> ORGANISM: Artificial Sequence
<220> FEATURE:
<223> OTHER INFORMATION: LILRB3 Heavy chain variable region CDR1 (9A1)

<400> SEQUENCE: 93

Ser Thr Phe Thr Gly Tyr Trp
1               5

<210> SEQ ID NO 94
<211> LENGTH: 8
<212> TYPE: PRT
<213> ORGANISM: Artificial Sequence
<220> FEATURE:
<223> OTHER INFORMATION: LILRB3 Heavy chain variable region CDR2 (9A1)

<400> SEQUENCE: 94

Ile Leu Pro Gly Ser Gly Tyr Thr
1               5

<210> SEQ ID NO 95
<211> LENGTH: 10
<212> TYPE: PRT
<213> ORGANISM: Artificial Sequence
<220> FEATURE:
<223> OTHER INFORMATION: LILRB3 Heavy chain variable region CDR3 (9A1)

<400> SEQUENCE: 95

Ala Arg Arg Glu Trp Tyr Tyr Phe Asp Tyr
1               5                   10

<210> SEQ ID NO 96
<211> LENGTH: 7
<212> TYPE: PRT
<213> ORGANISM: Artificial Sequence
```

```
<220> FEATURE:
<223> OTHER INFORMATION: LILRB3 Light chain variable region CDR1 (9A1)

<400> SEQUENCE: 96

Ser Ser Val Ser Ser Ser Tyr
1               5

<210> SEQ ID NO 97

<400> SEQUENCE: 97

000

<210> SEQ ID NO 98
<211> LENGTH: 9
<212> TYPE: PRT
<213> ORGANISM: Artificial Sequence
<220> FEATURE:
<223> OTHER INFORMATION: LILRB3 Light chain variable region CDR3 (9A1)

<400> SEQUENCE: 98

His Gln Tyr His Arg Ser Pro Phe Thr
1               5

<210> SEQ ID NO 99
<211> LENGTH: 8
<212> TYPE: PRT
<213> ORGANISM: Artificial Sequence
<220> FEATURE:
<223> OTHER INFORMATION: LILRB3 Heavy chain variable region CDR1 (1B2)

<400> SEQUENCE: 99

Gly Tyr Thr Phe Thr Val Tyr Trp
1               5

<210> SEQ ID NO 100
<211> LENGTH: 8
<212> TYPE: PRT
<213> ORGANISM: Artificial Sequence
<220> FEATURE:
<223> OTHER INFORMATION: LILRB3 Heavy chain variable region CDR2 (1B2)

<400> SEQUENCE: 100

Ile Leu Pro Gly Ser Gly Ser Ile
1               5

<210> SEQ ID NO 101
<211> LENGTH: 10
<212> TYPE: PRT
<213> ORGANISM: Artificial Sequence
<220> FEATURE:
<223> OTHER INFORMATION: LILRB3 Heavy chain variable region CDR3 (1B2)

<400> SEQUENCE: 101

Ala Arg Arg Thr Trp Tyr Tyr Phe Asp Tyr
1               5                   10

<210> SEQ ID NO 102
<211> LENGTH: 7
<212> TYPE: PRT
<213> ORGANISM: Artificial Sequence
<220> FEATURE:
<223> OTHER INFORMATION: LILRB3 Light chain variable region CDR1 (1B2)

<400> SEQUENCE: 102

Ser Ser Val Ser Ser Ser Tyr
1               5
```

-continued

```
<210> SEQ ID NO 103

<400> SEQUENCE: 103

000

<210> SEQ ID NO 104
<211> LENGTH: 9
<212> TYPE: PRT
<213> ORGANISM: Artificial Sequence
<220> FEATURE:
<223> OTHER INFORMATION: LILRB3 Light chain variable region CDR3 (1B2)

<400> SEQUENCE: 104

His Gln Tyr His Arg Ser Pro Phe Thr
1               5
```